US009267122B2

(12) United States Patent
DiPaolo et al.

(10) Patent No.: US 9,267,122 B2
(45) Date of Patent: Feb. 23, 2016

(54) MODULATION OF PHOSPHOLIPASE D FOR THE TREATMENT OF NEURODEGENERATIVE DISORDERS

(75) Inventors: Gilbert DiPaolo, Northford, CT (US); Tae-Wan Kim, East Brunswick, NJ (US); Tiago Gil Oliveira, Guimaraes (PT)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 13/305,422

(22) Filed: Nov. 28, 2011

(65) Prior Publication Data

US 2012/0178719 A1    Jul. 12, 2012

Related U.S. Application Data

(63) Continuation of application No. PCT/US2010/036660, filed on May 28, 2010.

(60) Provisional application No. 61/230,447, filed on Jul. 31, 2009, provisional application No. 61/182,609, filed on May 29, 2009.

(51) Int. Cl.
  *A61K 31/445* (2006.01)
  *A61K 31/415* (2006.01)
  *A61K 31/05* (2006.01)
  *C12N 9/20* (2006.01)
  *A61K 31/454* (2006.01)
  *A61K 31/4709* (2006.01)
  *G01N 33/92* (2006.01)

(52) U.S. Cl.
  CPC ............... *C12N 9/20* (2013.01); *A61K 31/454* (2013.01); *A61K 31/4709* (2013.01); *G01N 33/92* (2013.01); *G01N 2405/04* (2013.01); *G01N 2405/10* (2013.01); *G01N 2500/04* (2013.01); *G01N 2500/10* (2013.01)

(58) Field of Classification Search
  USPC ........ 514/17.8, 106, 879, 317, 320, 321, 387, 514/394, 733
  See application file for complete search history.

(56) References Cited

U.S. PATENT DOCUMENTS

| | | | | |
|---|---|---|---|---|
| 5,552,415 A * | 9/1996 | May | ............................. | 514/324 |
| 5,811,520 A | 9/1998 | Hawkins et al. | | |
| 2002/0102684 A1 | 8/2002 | Hawkins et al. | | |
| 2003/0113846 A1 | 6/2003 | Lal et al. | | |
| 2004/0005705 A1* | 1/2004 | Bennett et al. | ................ | 435/375 |
| 2007/0122807 A1 | 5/2007 | Alroy et al. | | |
| 2008/0300298 A1* | 12/2008 | Arbiser et al. | ................ | 514/450 |
| 2008/0312187 A1 | 12/2008 | Kim et al. | | |

FOREIGN PATENT DOCUMENTS

| | | | |
|---|---|---|---|
| CN | 101139267 | 3/2008 | |
| CN | 101411716 | 4/2009 | |
| EP | 0 304 330 | 2/1989 | |
| WO | WO 2006096415 A2 * | 9/2006 | ........... A61K 31/138 |
| WO | WO 2007/093807 | 8/2007 | |
| WO | WO 2007093807 A2 * | 8/2007 | ............ C07K 14/47 |
| WO | WO 2007/113266 | 10/2007 | |
| WO | WO 2008013764 A2 * | 1/2008 | ............ A61K 31/05 |
| WO | WO 2008/021368 | 2/2008 | |
| WO | WO 2008/064244 | 5/2008 | |
| WO | WO 2008074896 A1 * | 6/2008 | |
| WO | WO 2009/045481 | 4/2009 | |

OTHER PUBLICATIONS

Han, Y-S, et al. British Journal of Pharmacology vol. 141 pp. 997-1004. Published 2004.*
Denny, C. A., et al. Journal of Neurochemistry vol. 101, pp. 1294-1302. Published 2007.*
Suzuki, K. et al. Acta Neuropathol. vol. 114 pp. 481-489. Published 2007.*
Jenco, J.M., et al. Biochemistry vol. 37 pp. 4901-4909. Published 1998.*
Saito, Y, et al. Journal of Neuropathology and Experimental Neurology vol. 63, pp. 323-328. Published 2004.*
Jin, J-K., et al. Neuroscience Letters vol. 407, pp. 263-267. Published 2006.*
In re Bimeda Research and Development, Fed Circuit 2013.*
Santara v. Par Pharma, Court of Appeals Federal Circuit, 2012.*
Scott et al (Nature Chemical, Biology, vol. 5 pp. 108-117, published Jan. 11, 2009).*
International Search Report for PCT/US2010/036660 dated Aug. 4, 2010.
Scott et al. Design of Isofrom-selective phospholipase D. inhibitors that molecule cancer cell invasiveness. Nature Chemical Biology. Jan. 11, 2009 Vo. 5, p. 108-117; abstract, Fig. 1,2.
Su et al. 5-fluoro-2-indoly des-chlorohalopemide (FIPI), a phospholipase D pharmacological inhibitor that alters cell spreading and inhibits chemotaxis. Molecular Pharmacology, Dec. 2008, vol. 75 p. 437-446; abstract; p. 438, right col, para 4; p. 439, right col, para 3 (publication date for Su et al.).
Jin, et al., "Increased Expression of Phospholipase D1 in the Brains of Scrapie-Infected Mice", *Journal of Neurochemistry*, 92:452-461 (2005).

(Continued)

*Primary Examiner* — Paul Zarek
*Assistant Examiner* — George W Kosturko
(74) *Attorney, Agent, or Firm* — Baker Botts L.L.P.

(57) ABSTRACT

The present invention relates to methods of treating neurodegenerative diseases comprising administering, to a subject in need of such treatment, one or more agent that inhibits or reduces the action, including the catalytic activity, of an enzyme of the phospholipase D family, such as phospholipase D1 and/or phospholipase D2. The present invention also relates to cell-based assays which may be used to identify agents that inhibit or reduce the activity of enzymes of the phospholipase D family and that may be used in the treatment of neurodegenerative diseases.

8 Claims, 26 Drawing Sheets

(56) References Cited

OTHER PUBLICATIONS

Figure 1A:
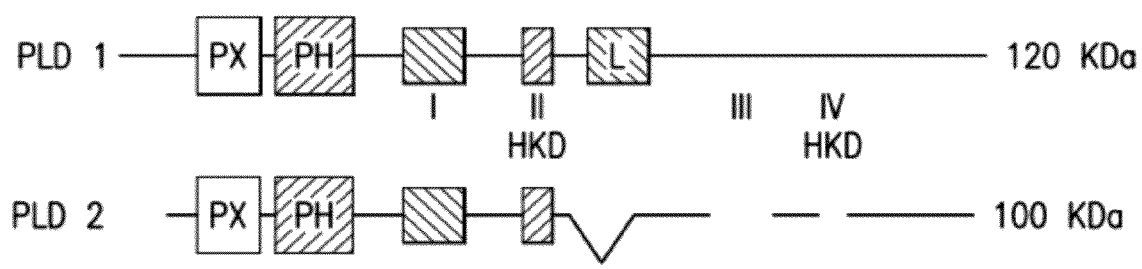

Cai, et al., "Phospholipase D1 Corrects Impaired BetaApp Trafficking and Neurite Outgrowth in Familial Alzheimer's Disease-Linked Presenilin-1 Mutant Neurons", *PNAS*, 103(6):1936-1940 (2006).

Jin, et al., "Phospholipase D1 is Up-Regulated in the Mitochondrial Fraction from the Brains of Alzheimer's Disease Patients", *Neurosci. Letters*, 407(3):263-267 (2006).

Jin, et al., "Phospholipase D1 is Associated with Amyloid Precursor Protein in Alzheimer's Disease", *Neurobiol. Aging*, 28(7):1015-1027 (2007).

Lavieri, et al., "Design and Synthesis of Isoform-Selective Phospholipase D (PLD) Inhibitors. Part II: Identification of the 1,3,8-Triazaspiro[4,5] Decan-4-One Priviledged Structure that Engenders PLD2 Selectivity", *Bioorganic & Medicinal Chemistry Letters*, 19:2240-2243 (2009).

Lewis, et al., "Design and Synthesis of Isoform-Selective Phospholipase D (PLD) Inhibitors. Part I: Impact of Alternative Halogenated Priviledged Structures for PLD1 specify", *Bioorganic & Medical Chemistry Letters*, 19:1916-1920 (2009).

Monovich, et al., "Optimization of Halopemide for Phospholipase D2 Inhibiton", *Bioorganic & Medicinal Chemistry Letters*, 17:2310-2311 (2007).

Oliviera, et al., "Phospholipase D2 Reduction ameliorates alzheimer's Disease-Linked Synaptic Dysfunction and Cognitive Deficits", Abstract from Society for Neurosciences, (2010).

Buck, "Synthesis of Halopemide Analogs for the Specific and Non-Specific Inhibition of Phospholipase D", *41st Western Regional Meeting of the American Chemical Society*, Abstract, 2007.

* cited by examiner

Trans-diethylstilbestrol (1)

SCH4207 89 (4)

Halopemide (8)

Honokiol (3)

Resveratrol (2)

Raloxifene (6)

Presqualene diphosphate (5)

| Compound | R | PLDC2 IC$_{50}$ ($\mu M$) |
|---|---|---|
| 1 | p-FPh | 1.500 |
| 4a | p-FPh | 1.410 |
| 4b | Ph | 1.500 |
| 4h | 3-Thienyl | 1.000 |
| 4i | 3-Quinolinyl | 0.600 |
| 4j | 2-Indolyl | 0.020 |
| 4k | 5-Fluoro-2-indolyl | 0.020 |
| 4m | 2-Benzthienyl | 2.000 |

4k

Dual PLD1/2 inhibitor, 2

PLD1 inhibitor, 3          PLD1 inhibitor, 4

PLD2 inhibitor, 5

R¹ substituents for "11" series molecules

R¹ and X substituents for "12" series compounds:

| Cmpd | X | R¹ |
|---|---|---|
| 1 | 5-Cl | 4-F-phenyl |
| 12a | 5-Cl | 4-methyl-phenyl |
| 12b | 5-Cl | trans-2-phenylcyclopropyl |
| 12c | 5-F | 2-naphthyl |
| 12d | 5-F | 4-Cl-phenyl |
| 12e | 5-F | 4-F-phenyl |
| 12f | 5-Br | 4-Cl-phenyl |
| 12g | 5-Br | 4-F-phenyl |
| 12h | 6-F | 4-Cl-phenyl |
| 12i | 6-F | 3,4-di-F-phenyl |

R¹ and X substituents for "13" series compounds:

| Cmpd | X | R¹ |
|---|---|---|
| 3 | 5-Cl | 2-naphthyl |
| 13a | 4-F | 4-chlorophenyl |
| 13b | 4-F | 4-fluorophenyl |
| 13c | 4-F | 3,4-difluorophenyl |
| 13d | 4-F | 2-naphthyl |
| 13e | 4-F | trans-2-phenylcyclopropyl |
| 13f | 5-F | 4-fluorophenyl |
| 13g | 5-F | 4-chlorophenyl |

R¹ and X substituents for "13" series compounds:

| Cmpd | X | R¹ |
|---|---|---|
| 13h | 5-Cl | 4-F-phenyl |
| 13i | 5-Cl | 4-Cl-phenyl |
| 13J | 5-Cl | trans-2-phenylcyclopropyl |
| 13k | 5-Cl | 3,4-difluorophenyl |
| 13l | 5-Br | 3,4-difluorophenyl |
| 13m | 5-Br | 2-naphthyl |

R¹ and X substituents for "13" series compounds:

| Cmpd | X | R¹ |
|---|---|---|
| 13n | 5-Br | 4-chlorophenyl |
| 13o | 5-F | trans-2-phenylcyclopropyl |
| 13p | 6-F | 2-naphthyl |
| 13q | 6-F | trans-2-phenylcyclopropyl |

R¹ substituents for compounds of the "9" series:

| Cmpd | R¹ |
|---|---|
| 3 | 2-naphthyl |
| 9a | 2-phenylcyclopropyl |
| 9b | 3-quinolinyl |
| 9c | phenylethynyl |
| 9d | 2-benzothiophenyl |
| 9e | 2-tetrahydronaphthyl |
| 9f | 4-(2-amino-3-methoxyphenyl) / 2-amino-5-substituted-methoxyphenyl (OMe, NH₂) |
| 9g | 2-quinoxalinyl |

R¹ substituents for compounds of the "10" series:

| Cmpd | R¹ |
|---|---|
| 10a | 2-naphthyl |
| 10b | trans-2-phenylcyclopropyl |
| 10c | 3,4-difluorophenyl |
| 10d | 3-methylphenyl |

MODULATION OF PHOSPHOLIPASE D FOR THE TREATMENT OF NEURODEGENERATIVE DISORDERS

CROSS REFERENCE TO RELATED APPLICATIONS

The present application is a continuation of International Patent Application No. PCT/US2010/036660, filed May 28, 2010, published in English on Dec. 2, 2010 as International Patent Publication No. WO10/138,869, and claims priority to U.S. Provisional Application No. 61/182,609, filed May 29, 2009, and U.S. Provisional Application No. 61/230,447, filed Jul. 31, 2009, all three of which are incorporated by reference herein in their entireties.

This invention was made with government support under NIH RO1 NS056049 awarded by the National Institutes of Health. The government has certain rights in the invention.

1. INTRODUCTION

The present invention relates to methods of treating neurodegenerative diseases comprising administering, to a subject in need of such treatment, one or more agent that inhibits or reduces the action, including the catalytic activity, of an enzyme of the phospholipase D family, such as phospholipase D1 and/or phospholipase D2. The present invention also relates to cell-based assays which may be used to identify agents that inhibit or reduce the activity of enzymes of the phospholipase D family and that may be used in methods of treating neurodegenerative diseases.

2. BACKGROUND OF THE INVENTION

Neurodegenerative diseases encompass a variety of disorders characterized by synaptic dysfunction, associated with a progressive decline in cognitive and functional abilities, often resulting in death. Alzheimer's disease (AD) is the most common age-associated debilitating neurodegenerative disorder, affecting approximately 4 million Americans and about 20-30 million people worldwide. The classical neuropathological features of AD include the presence of senile (β-amyloid-containing) plaques and neurofibrillary tangles in the hippocampus, the amygdala, and the association cortices of the temporal, frontal and parietal lobes. More subtle changes include reactive astrocytic changes, as well as the loss of neurons and synapses in the entorhinal cortex and basal forebrain.

The pathogenesis of Alzheimer's Disease is not fully understood, however it is known that there is an association between the disease and a cleavage product of the membrane protein, Amyloid Precursor Protein (APP). γ-secretase mediates the C-terminal cleavage of the amyloid-β (Aβ) domain of APP, thereby liberating Aβ/p3 from membrane-bound APP C-terminal fragments generated through ectodomain shedding by α-(ADAM10 and TACE) or β-secretase (BACE1). γ-secretase cleavage generates two major Aβ isoforms—Aβ40 and Aβ42. It has been well documented that all mutations in presenilin genes PS1 and PS2 result in modulation of γ-secretase activity, leading to an elevation in the generation of the highly amyloidogenic and neurotoxic Aβ42 species, possibly at the expense of the more benign Aβ40 peptide.

Phosphoinositides ("PIs") serve as signaling molecules in a diverse array of cellular pathways (Williams, 1999, Biochim. Biophys. Acta 1441: 255-267; Rhee and Bai, 1997, J. Biol. Chem. 272(24): 15045-15048; Katan, 1998. Biochim. Biophys. Acta 1436: 5-17) and aberrant regulation of PIs in certain cell types has been shown to promote various human disease states (Pendaries et al., 2003, FEBS Lett. 546(1):25-31 PI signaling is tightly regulated by a number of kinases, phosphatases, and phospholipases. The hydrolysis of phosphotidylinositol 4,5-biphosphate (PIP2) by phospholipase C(PLC) is an early and key event in the regulation of a variety of cell functions. It has been discovered that Aβ42 causes a decrease in PIP2 levels (see International Patent Application No. PCT/US2007/085274, WO 2008/064244, incorporated by reference herein).

Phospholipase D (PLD) catalyzes the hydrolysis of phosphatidylcholine to form phosphatidic acid (see International Patent Application No. PCT/US2007/085274, WO 2008/064244, incorporated by reference herein; Sweeney et al., 2002, J. Biol. Chem. 277:3030-3039; Exton et al., 2002, FEBS Lett 531:58-61; Schields and Aryan, 1999, Curr. Opin. Cell Biol. 11:489-494). PLD has been reported to regulate various membrane trafficking steps (e.g., the release of secretory vesicles, endocytosis and exocytosis (Chen et al., 1997, J. Cell Biol. 138:495-504; Shen et al., 2001, Mol. Cell. Biol. 21:595-602; Humeau et al., 2001, Proc. Natl. Acad. Sci. 98:15300-'5305; Cockcroft, 2001, Cell. Nol. Life Sci. 58:1674-1687). PLD1 and PLD2 are two different isoforms of this enzyme (Hammond et al., 1995, J. Biol. Chem. 270: 29640; Colley et al., 1997, Curr. Biol. 7:191; Steed et al., 1998, FASEB J. 12:1309; see FIG. 1A-B) and are reported to have different cellular functions (Choi et al., 2002, J. Immunol. 168:5682-5689). Cai et al., 2006, Proc. Natl. Acad. Sci. U.S.A. reports that PLD1 regulates intracellular trafficking of βAPP and its companion paper (Cai et al., 2006, Proc. Natl. Acad. Sci. U.S.A. 103:1941-1946) reports that through an independent mechanism PLD1 compromises the integrity of the γ secretase complex, inhibiting β-amyloid formation. Cai et al suggest that defects in PLD metabolism may contribute to Alzheimer's Disease pathogenesis.

3. SUMMARY OF THE INVENTION

The present invention relates to methods of treating neurodegenerative diseases comprising administering, to a subject in need of such treatment, one or more agent that inhibits or reduces the action, including the catalytic activity, of an enzyme of the phospholipase D family, such as phospholipase D1 and/or phospholipase D2. The present invention also relates to cell-based assays which may be used to identify agents that inhibit or reduce the activity of enzymes of the phospholipase D family.

In further embodiments, the present invention provides for treatment of disorders involving increased levels of gangliosides, based upon the discovery that PLD inhibitors, preferably PLD2 inhibitors, decrease ganglioside levels.

Treating, as that term is used herein, refers to ameliorating or reducing or decreasing the rate of progression of a symptom or sign of the disease or decreasing the risk of developing the disease or disorder, including, but not limited to, impaired memory (short or long-term) and/or dementia. Non-limiting examples of neurodegenerative diseases which may be treated according to the invention include Alzheimer's Disease, Mild Cognitive Impairment, Parkinson's Disease, Huntington's chorea, senile dementia and Creuzfeld-Jacob diseases. The present invention may also be used to inhibit progressive memory impairment. Non-limiting examples of disorders having increased levels of gangliosides that may be treated according to the invention include GM1 gangliosidosis, Morquio B disease, Tay-Sachs disease, Sandhoff disease, AB variant, and Niemann-Pick disease type C.

4. BRIEF DESCRIPTION OF THE FIGURES

Figure 1B:
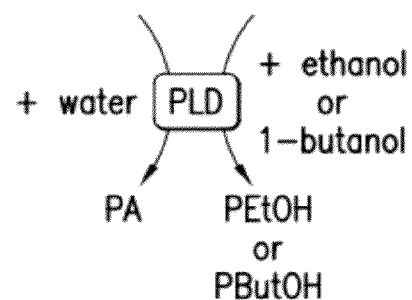

FIG. 1A-B. (A) Domain structure of PLD1/PLD2. (B) The transphosphatidylation reaction mediated by PLD enzymes, which leads to the synthesis of phosphatidylethanol (PEtOH) or phosphatidylbutanol (PButOH) in the presence of ethanol and 1-butanol, respectively.

FIG. 2A-D (A) Levels of diphosphoglycerate ("DPG"), PEtOH, phosphatidylinositol 4 phosphate ("PtdIns4P") and PIP2 (also "PtdIns(4,5)P$_2$) in primary cortical neurons treated with 200 nM synthetic oAβ42 (n=9). (B) PLD activity, as measured by the synthesis of [3H]-phosphatidylbutanol via a transphosphatidylation reaction in the presence of 1-butanol, in cultured primary cortical neurons in the presence of absence of oAβ42 or 2 μM Ca++ ionophore ionomycin. C) PLD activity, as measured by the synthesis of [3H]phosphatidylbutanol, in cultured N2a cells in the presence of absence of oAβ42. (D) PLD activity, as measured by to the synthesis of [3H]phosphatidylbutanol, in either cultured N2a cells of cultured N2a cells expressing the swAPP mutant. (E) PLD2 activity, as measured by [$^3$H]phosphatidylbutanol production, in response to oAβ42 in primary neuron cortical cultures prepared from mice that are wild-type (+/+) or heterozygous (+/−) or homozygous (−/+) mutants in PLD2. Values denote means±SEM. ns—non significant. * p<0.05;  p<0.01; * p<0.001

FIG. 3A-D. Aβ-induced relocalization of GFP-PLD2 in PC12 cells. (A) Calculation of the plasma membrane/cytoplasm ratio; (B) Quantification of the effects of 200 nM synthetic oligomeric Aβ42. Control (n=31 cells); 5 min (n=29); 30 min (n=32) and 120 min (n=30). (C) The relocalization of GFPPLD2 is Ca2+-dependent. control (n=12); 200 nM Aβ42 (n=13); 200 nM reversed peptide Aβ42-1 (n=12); 2 μM ionomycin (n=13); 2 mM EGTA (n=14); 2 mM EGTA and 200 nM oAβ42 (n=13). All the treatments were 30 min long. D. PLD2-GFP construct.

Figure 4A:
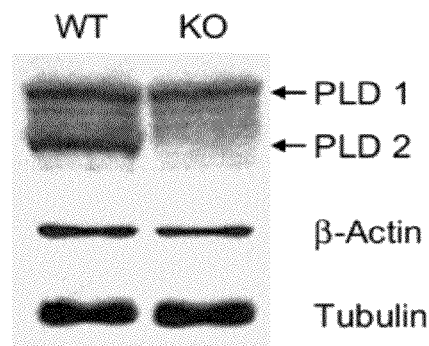
Figure 4B:
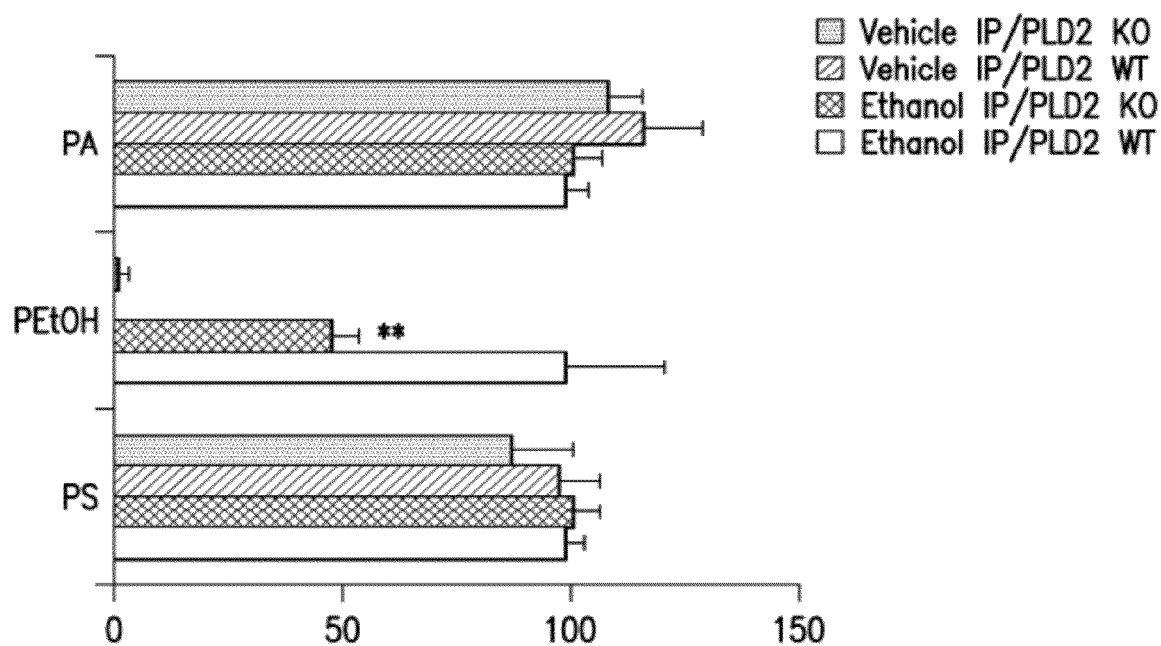

FIG. 4A-B. (A) PLD2 immunoreactivity is absent in adult brain extracts (postnuclear supernatants) prepared from Pld2 KO mice. The Western blot analysis was performed using ECL with antibodies directed to the indicated proteins. (B) Decreased total PLD activity in Pld2 KO brain, as measured by phosphatidylethanol (PEtOH) production following an I.P. injection of ethanol into the mice. PEtOH was measured by LC-MS. The levels of phosphatidylserine are shown as a control. N=4.

Figure 5A:
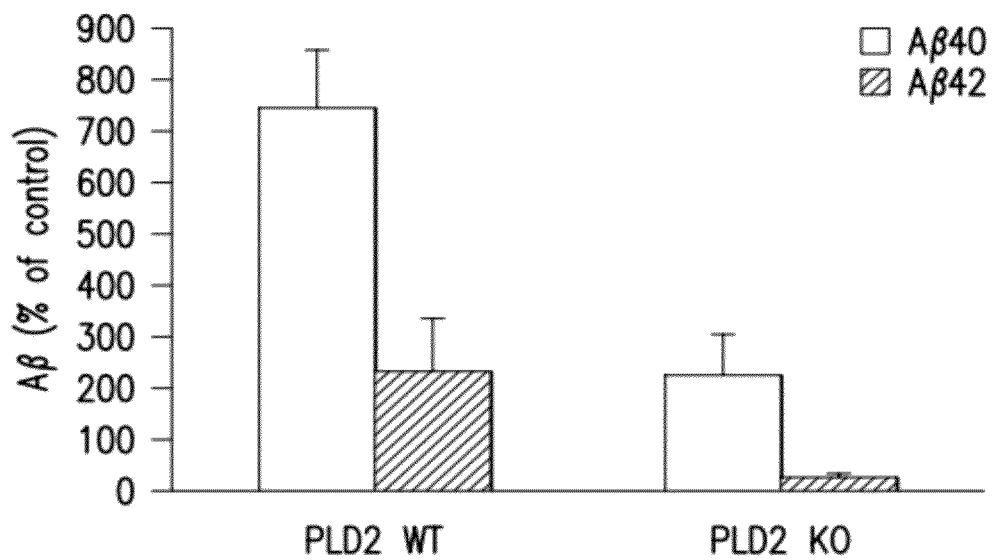
Figure 5B:
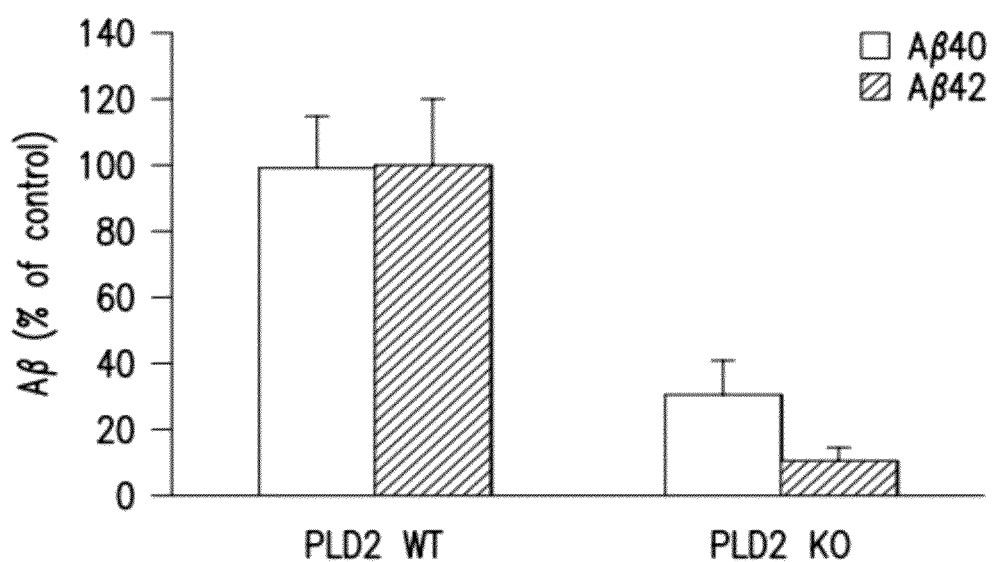

FIG. 5A-B. Decreased levels of secreted Aβ in Pld2 KO cortical neurons. Cultures were infected with a swAPP-lentivirus at day 14 and the media were collected at day 16 for ELISA measurements of Aβ40 and Aβ42. (A) Aβ levels normalized to total protein and expressed as % of non-infected Pld2 WT cultures. (B) Normalized Aβ40 and Aβ42 levels (% WT). N=3.

Figure 6:
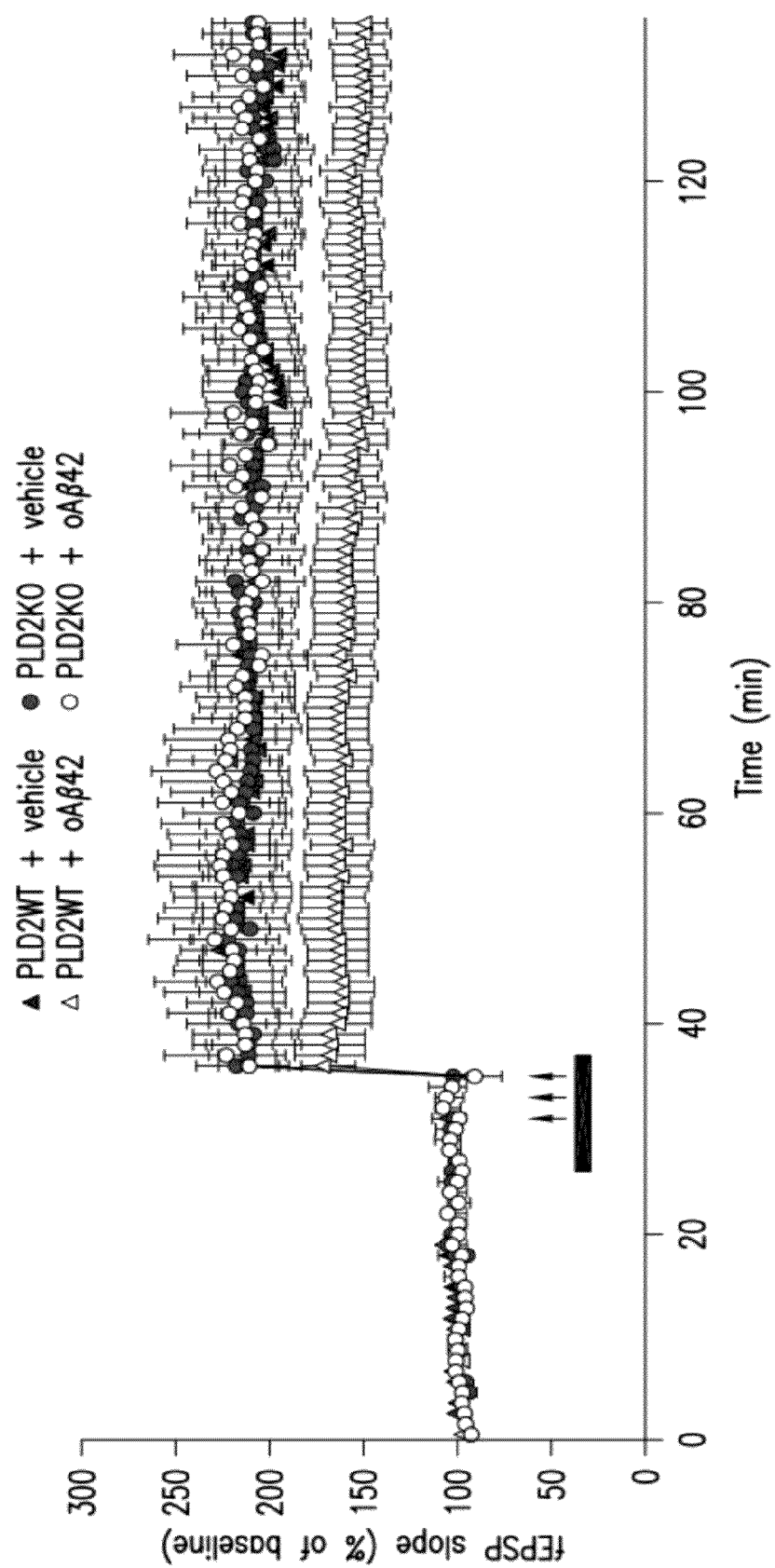

FIG. 6. Hippocampi from PLD2KO mice show normal LTP in the presence of oAβ42. There was no difference in LTP between PLD2WT slices (n=10) and PLD2KO slices (n=9) in the presence of vehicle (F1,17=0.00, p=0.947). Although PLD2WT slices showed a reduction of LTP following bath application of 200 nM oAβ42 (n=8) (F1,16=5.19, p=0.038, relative to vehicle), PLD2KO slices showed no LTP differences in the presence of the peptide (n=8) (F1,14=0.01, p=0.919, relative to vehicle). fEPSP, CA1 field-excitatory postsynaptic potential. The bar represents the time of bath application of oAβ42. The three arrows represent the .-burst stimulation used to induce potentiation. Animals were approximately 3 months old.

Figure 7:
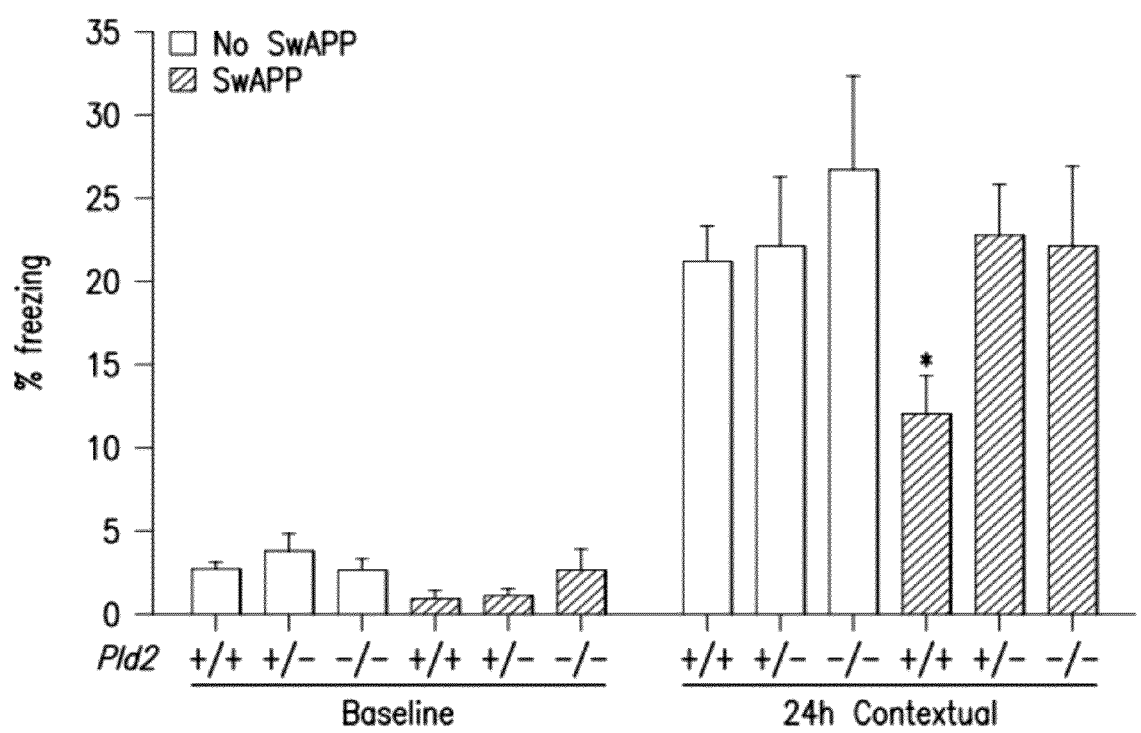

FIG. 7. PLD2 ablation improves learning and memory in SwAPP mice. SwAPP mice (Tg2576) were crossed with Pld2 knockout mice and the resulting offspring [Pld2+/+/no tg (n=14); Pld2+/−/no tg (n=14); Pld2−/−/no tg (n=11); Pld2+/+/SwAPP (n=10); Pld2+/−/SwAPP (n=12); Pld2−/−/SwAPP (n=11)] were subjected to training for contextual fear memory which was assessed 24 h after the foot shock, using 5-6 month old animals. *, p<0.05 in Student's one-tail t-test.

Figure 8:
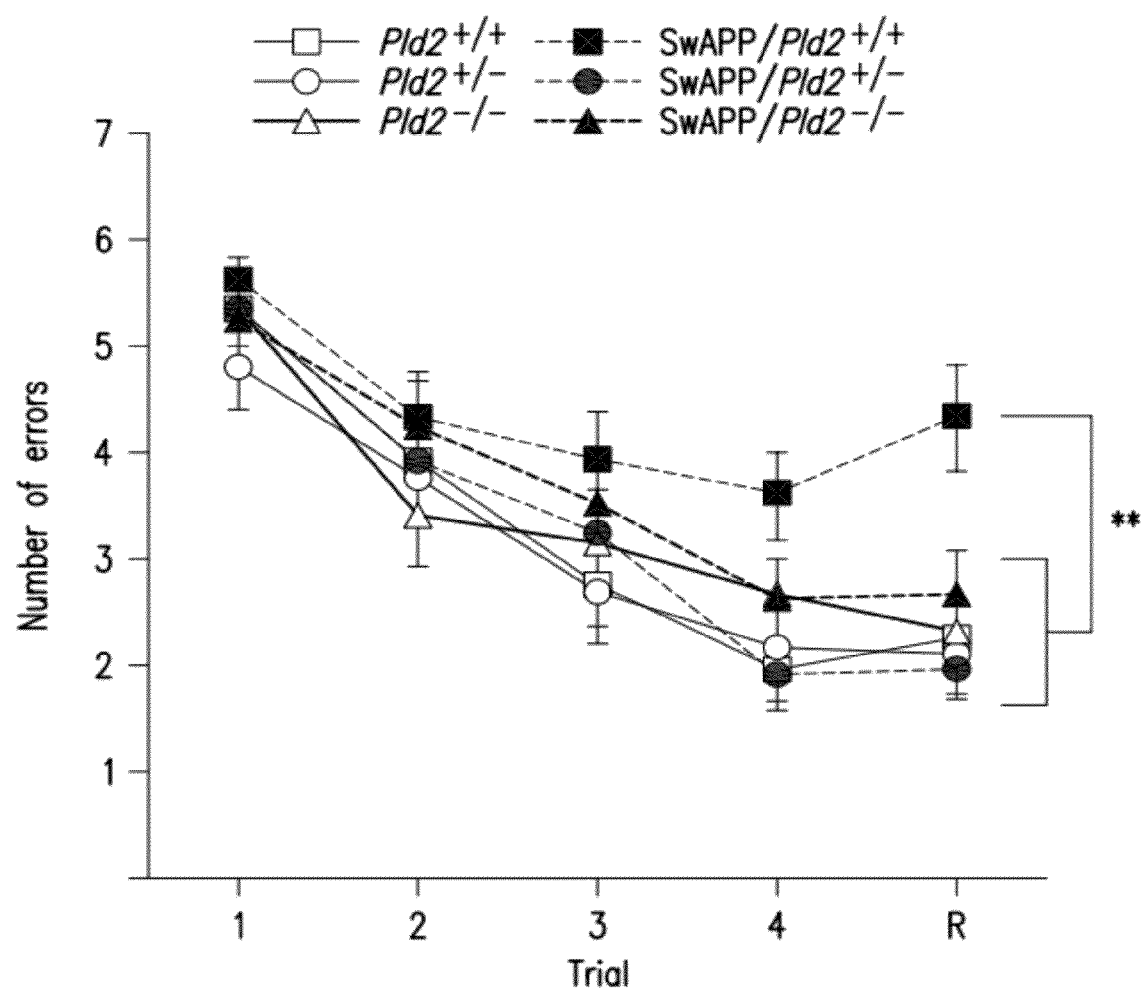

FIG. 8. PLD2 ablation improves learning and memory in SwAPP mice. Twelve month-old mice were subjected to Radial Arm Water Maze (RAWM) testing. Errors were scored in the last 3 days of testing. The n value was 8 for all the genotypes, except for Pld2−/−/SwAPP (n=7) and Pld2+/+/SwAPP (n=6). **, p<0.01. Values denote means±SEM.

FIG. 9A-E. (A) FIPI partially rescues oAβ42 induced decrease in PIP2 levels. Two week old primary cortical neuronal cultures were acutely treated either vehicle ("1"), 200 nM oAβ42 for 2 hours ("2"), 750 nM FIPI for 3 hours ("3") or pretreatment with 750 nM FIPI for 1 hour followed by treatment with 200 nM oAβ42 for 2 hours ("4"). n=3. (B) PLD1 and PLD2 levels in mice that are wild-type or homozygous mutants in PLD2, ±SwAPP. (C) Relative amounts of PA species in mutant mice as indicated versus control. Values denote mean±SEM (n=6-8). * p<0.05;  p<0.01; * p<0.001. (D) GM3 levels in mice that are wild-type or homozygous mutants in PLD2, SwAPP (color version); (E) GM3 levels in mice that are wild type or homozygous mutants in PLD2, ±SwAPP (black and white simplification of FIG. 9D; cross-hatching to show color: ///=green, \\\=red, gradations of color not shown).

Figure 10A:
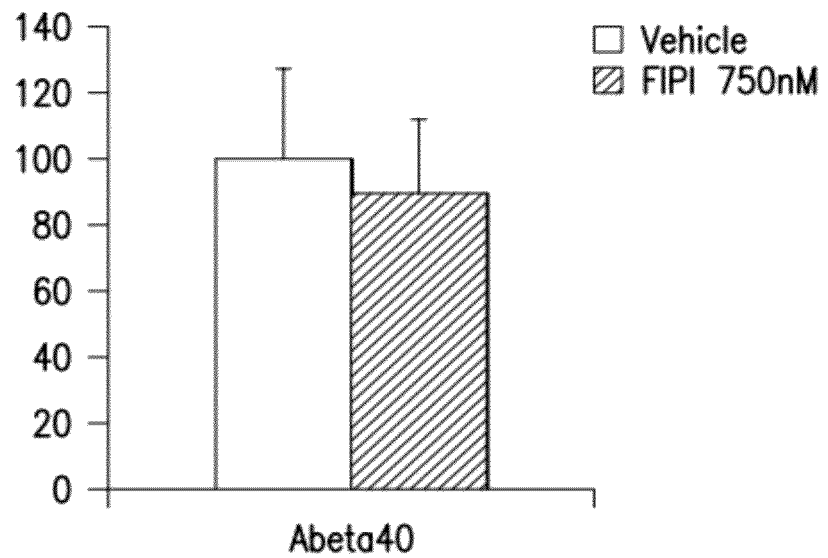
Figure 10B:
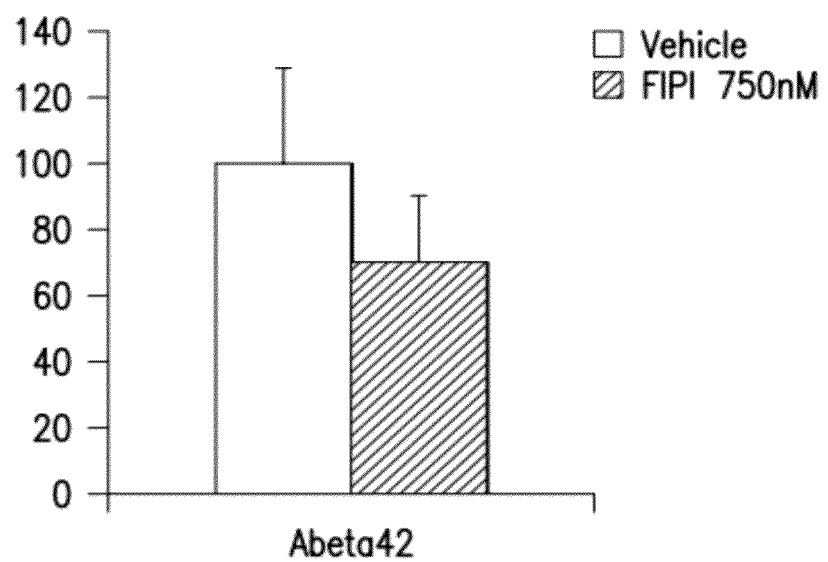

FIG. 10A-B. FIPI induced decrease production of Aβ. N2a cells expressing swAPP after reaching confluence, were replaced with new media and treated either with vehicle (black) or FIPI (gray) for 6 hours. The media was collected and both Aβ40 (A) and Aβ42 (B) were measured by ELISA. n=6.

FIG. 11A-M. PLD inhibitors.

5. DETAILED DESCRIPTION OF THE INVENTION

The present invention relates to the use of agents that reduce the production of amyloid beta and/or that inhibit the toxic effects of amyloid beta by inhibiting or reducing the action, including the catalytic activity, of enzymes of the phospholipase D family, such as phospholipase D1 (PLD1) and/or phospholipase D2 (PLD2), including the use of such agents for the treatment of neurodegenerative diseases. The present invention also relates to assay systems which may be used to identify agents that inhibit or reduce the action and/or activity of enzymes of the phospholipase D family and that may be used in the methods of treatment described herein.

For purposes of clarity, and not by way of limitation, the detailed description of the invention is divided into the following subsections:
 (i) PLD inhibitors;
 (ii) assay systems; and
 (iii) methods of treatment.

5.1 PLD Inhibitors

Inhibitors of PLD activity, including PLD 1 and PLD2 inhibitors, may be used according to the invention. A PLD inhibitor decreases the amount of PLD activity present in the subject to which it is administered, and may do so by any mechanism, including direct inhibition of enzyme activity as well as reduction in the amount or availability of PLD.

In certain non-limiting embodiments, the invention provides for the use of an agent that inhibits the enzyme activity of PLD, which may be PLD1 and/or PLD2, although inhibition of PLD2 is preferred.

In one non-limiting embodiment, an agent that inhibits PLD including PLD2 is 5-Fluoro-2-indolyl des-chlorohalopemide ("FIPI").

Figure 11A:
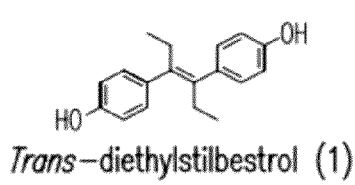
Figure 11A:
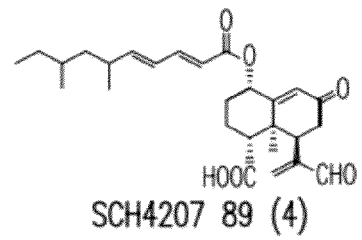
Figure 11A:
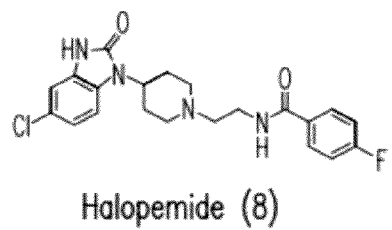
Figure 11A:
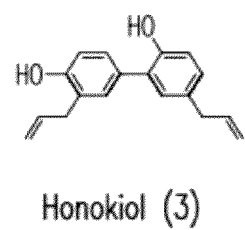
Figure 11A:
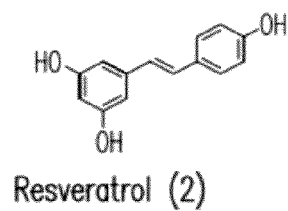
Figure 11A:
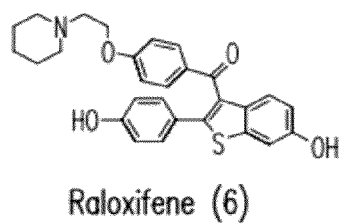
Figure 11A:
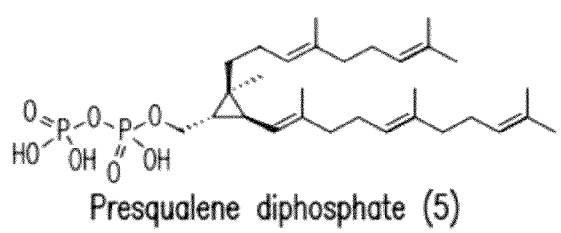
Figure 11B:
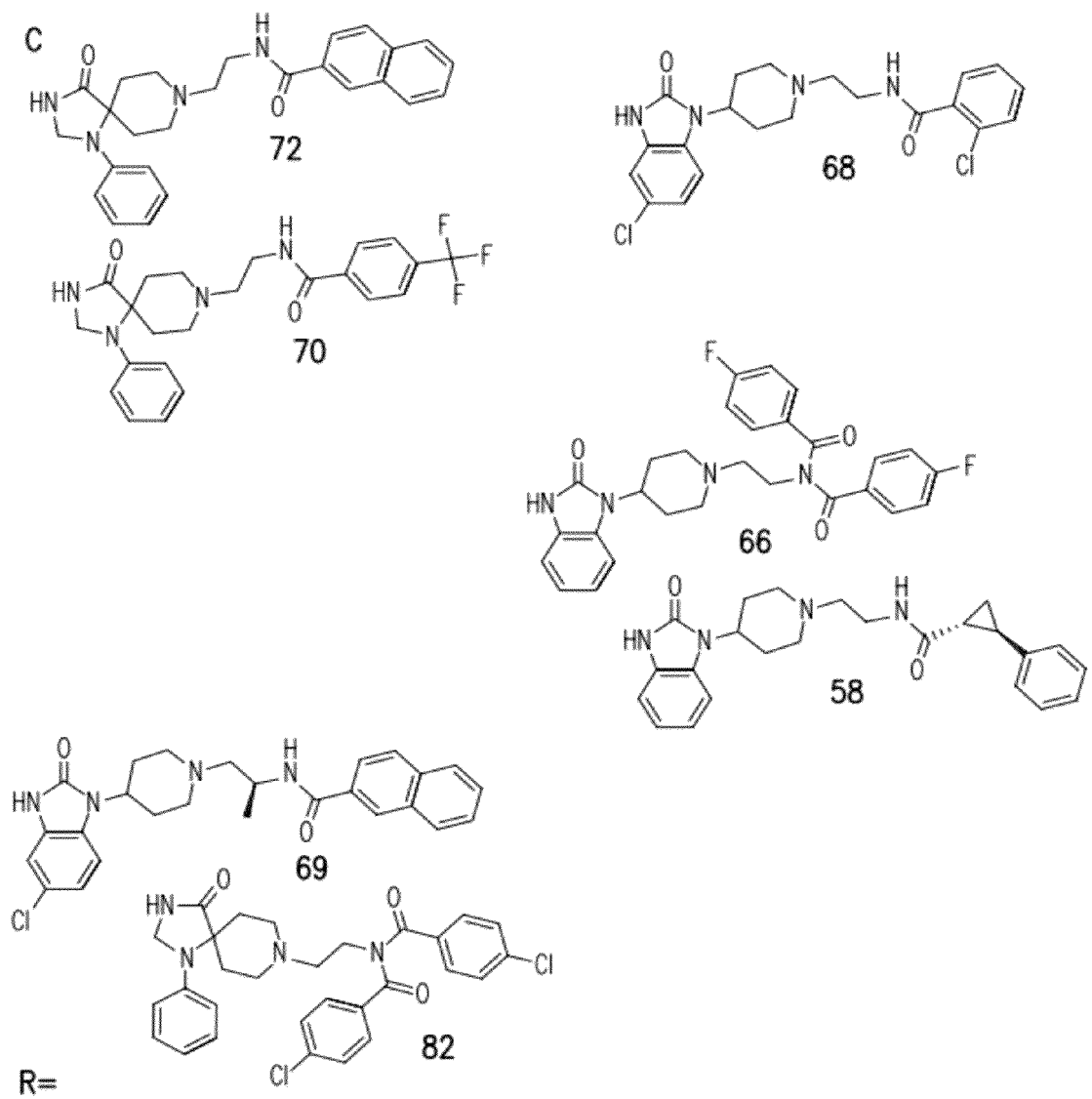
Figure 11C:
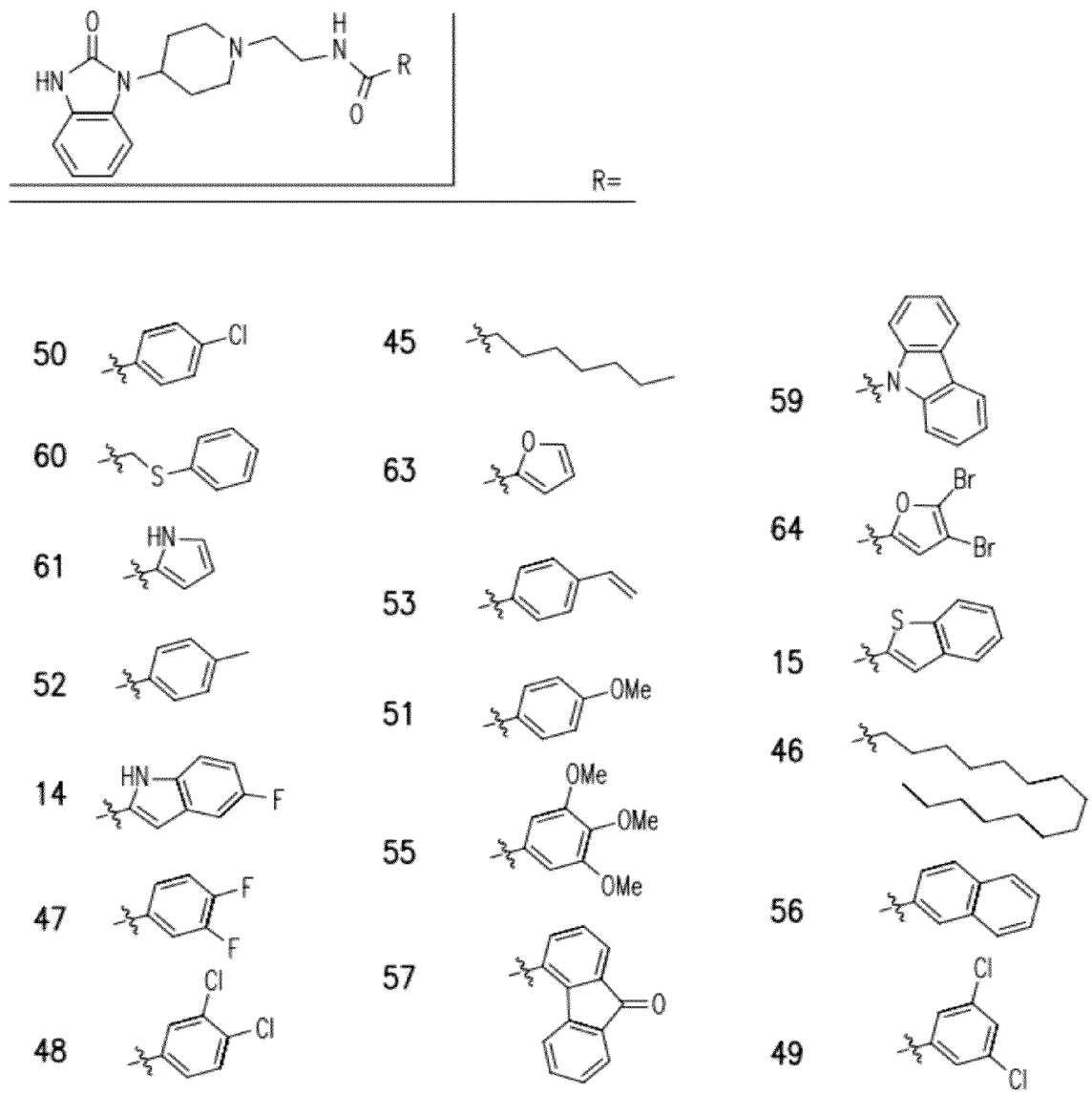
Figure 11D:
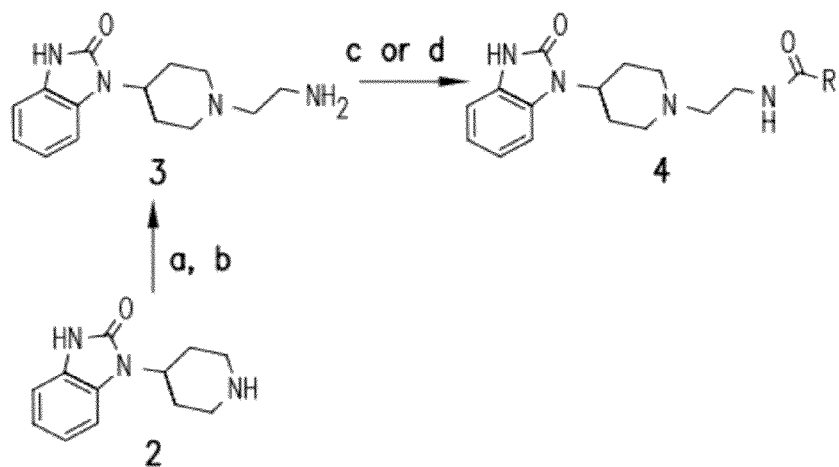
Figure 11D:
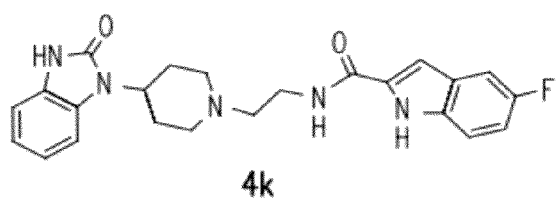
Figure 11E:
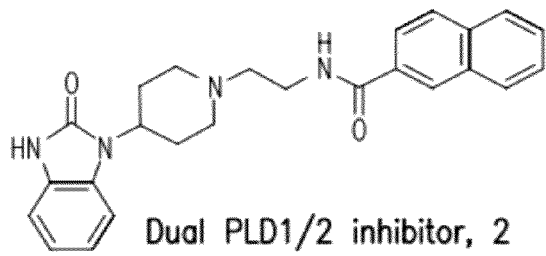
Figure 11E:
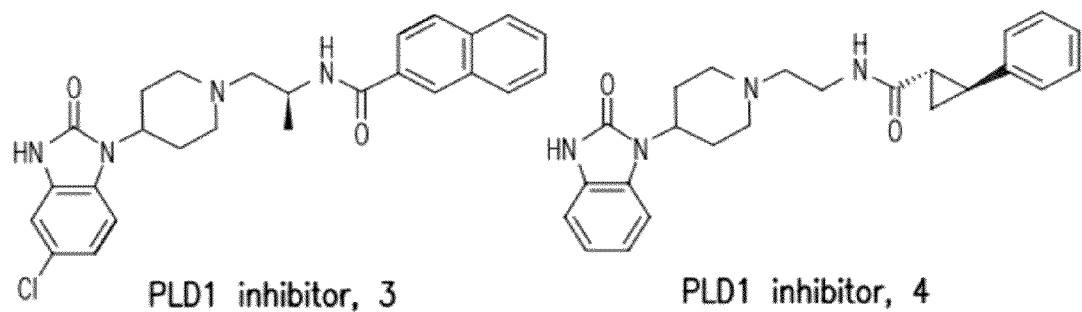
Figure 11E:
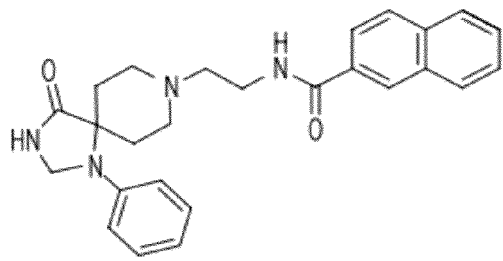
Figure 11F:
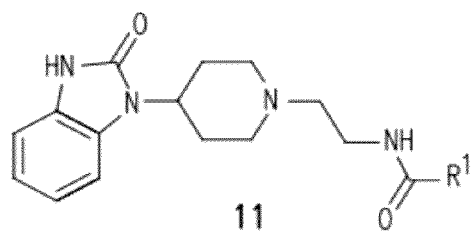
Figure 11G:
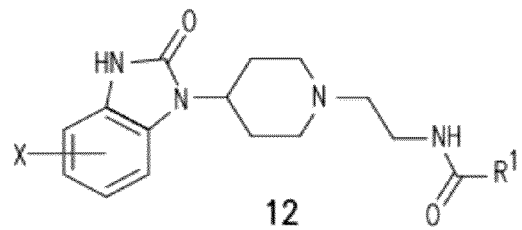
Figure 11H:
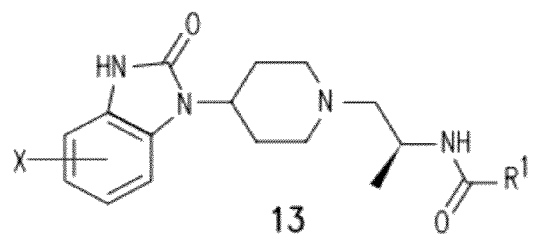
Figure 11I:
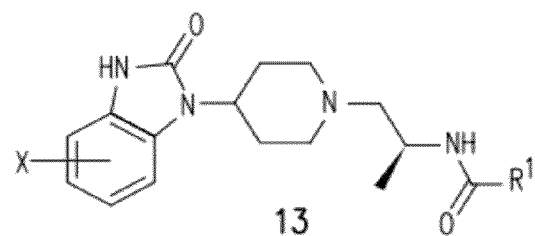

Additional PLD inhibitors, which may be used according to the invention include, but are not limited to: diethylstibestrol, resveratrol, honkiol, SCH420789, presqualene diphosphate, raloxifene, halopemide, 4-hydroxy tamoxifen, compounds depicted in FIGS. 11A-C (Scott et al., 2009, Nat Chem Biol 5(2):108-117 and its supplemental information online at Nature Chemical Biology 10.1038/nchembio.140); halopemide derivatives, especially halopemide derivatives comprising a 2-indolyl moiety, including compounds set forth in FIG. 11D (Monovich et al., 2007, Bioorg. Med. Chem. Lett. 17:2310-2311); compounds shown in FIGS. 11E-J including, but not limited to, halopemide derivatives comprising a halogenated piperidinyl benzimidazolone moiety and a S-methyl moiety (Lewis et al., 2009, Bioorg. Med. Chem. Letts. 19:1916-1920); derivatives of compound 5 of FIG. 11E, including compounds that comprise a 1,3,8-triazaspiro[4,5]decan-4-one structure, including compounds depicted in FIG. 11K-L (Lavieri et al., 2009, Bioorg. Med. Chem. Lett. 19:2240-2243); and compounds depicted in FIG. 11M (Lavieri et al., 2009, Bioorg. Med. Chem. Lett. 19:2240-2243).

In particular, preferred non-limiting embodiments, the PLD inhibitor is a PLD2 selective inhibitor such as, but not limited to, 4-OH tamoxifen; compounds 72 and 82 of FIG. 11B (Scott et al., 2009, Nat Chem Biol 5(2): 108-117); compounds 4j and 4k of FIG. 11D (Monovich et al., 2007, Bioorg. Med. Chem. Lett. 17:2310-2311); compound 5 of FIG. 11E (Lewis et al., 2009, Bioorg. Med. Chem. Letts. 19:1916-1920); and derivatives of compound 5 of FIG. 11E, including compounds that comprise a 1,3,8-triazaspiro[4,5]decan-4-one structure, including compounds depicted in FIG. 11K-L (Lavieri et al., 2009, Bioorg. Med. Chem. Lett. 19:2240-2243). Each of the foregoing references and any publicly supplied supplemental information linked thereto, and any compounds and/or synthetic schemes set forth therein, are incorporated by reference in their entireties herein.

In another preferred, non-limiting embodiment of the invention, the PLD inhibitor is compound 56 of FIG. 11C (which is also the Dual PLD1/2 inhibitor 2 of FIG. 11E and compound 2 of FIG. 11F), also known as N-(2-(4-(2-oxo-2,3-dihydro-1H-benzo[d]imidazol-1-yl)piperidin-1-yl)ethyl)-2-napthamide, which has a PLD1 $IC_{50}$ of 81 nM, a PLD2 $IC_{50}$ of 240 nM, a 293-PLD2 $IC_{50}$ of 380 nM, and a Calu-1 $IC_{50}$ of 21 nM (Scott et al., 2009, Nature Chemical Biology 5:108-117.

Figure 11J:
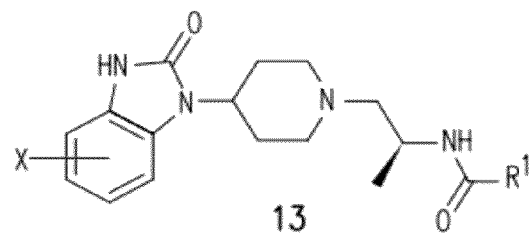
Figure 11J:
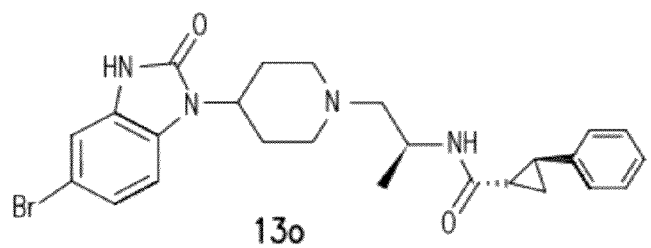

In another preferred, non-limiting embodiment of the invention, the PLD inhibitor is compound 13r of FIG. 11J, also, known as (1R,2R)—N—((S)-1-(4-(5-bromo-2-oxo-2,3-dihydro-1H-benzo[d]imidazol-1-yl)piperidin-1-yl)propan-2-yl)-2-phenylcyclopropanecarboxamide, which has a PLD1 $IC_{50}$ of 15 nM, a PLD2 $IC_{50}$ of 1100 nM, a 293-PLD2 $IC_{50}$ of 6400 nM, and a Calu-1 $IC_{50}$ of 3.7 nM (Lewis et al., 2009, Bioorganic and Medicinal Chemistry Letters 19:1916-1920); this compound is PLD1 selective.

Figure 11K:
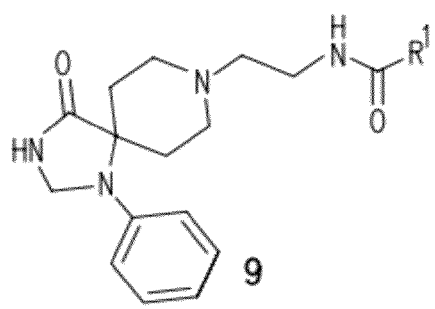
Figure 11L:
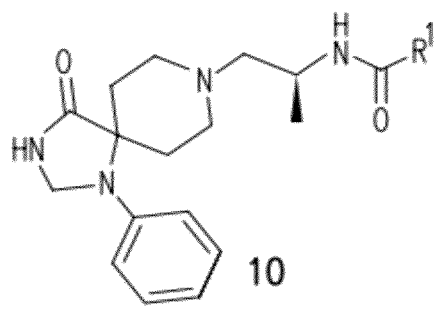
Figure 11M:
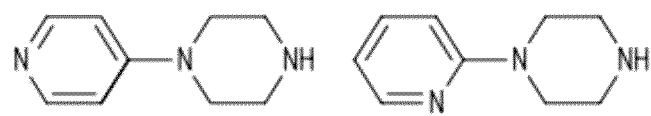

In another preferred, non-limiting embodiment of the invention, the PLD inhibitor is compound 9b of FIG. 11K, also known as N-(2-(4-oxo-1-phenyl-1,3,8-triazaspiro[4,5] decan-8-yl)ethyl)quinoline-3-carboxamide, which has a PLD1 $IC_{50}$ of 20,000 nM, a PLD2 $IC_{50}$ of 500 nM, a 293-PLD2 $IC_{50}$ of 90 nM, and a Calu-1 $IC_{50}$ of 1900 nM (Lavieri et al., 2009, Bioorganic and Medicinal Chemistry Letters 19:2240-2243); this compound is PLD2 selective.

Additional PLD inhibitors may be identified by methods known in the art, including, but not limited to, the assays set forth in Scott et al., 2009, Nat Chem Biol. February; 5(2): 108-17; Monovich et al., 2007, Bioorg. Med. Chem. Lett. 17:2310-2311; Lewis et al., 2009, Bioorg. Med. Chem. Letts. 19:1916-1920; or Lavieri et al., 2009, Bioorg. Med. Chem. Lett. 19:2240-2243.

Alternatively, a PLD inhibitor may be a molecule which decreases expression of PLD, and especially PLD2, for example a small interfering RNA or an antisense RNA comprising a portion complementary to the PLD1 and/or PLD2 gene.

5.2 Assay Systems

Figure 3A:
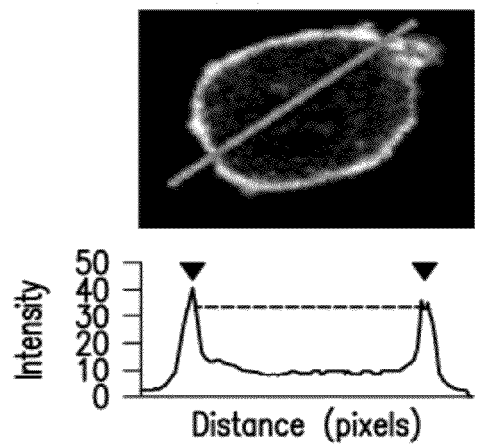
Figure 3B:
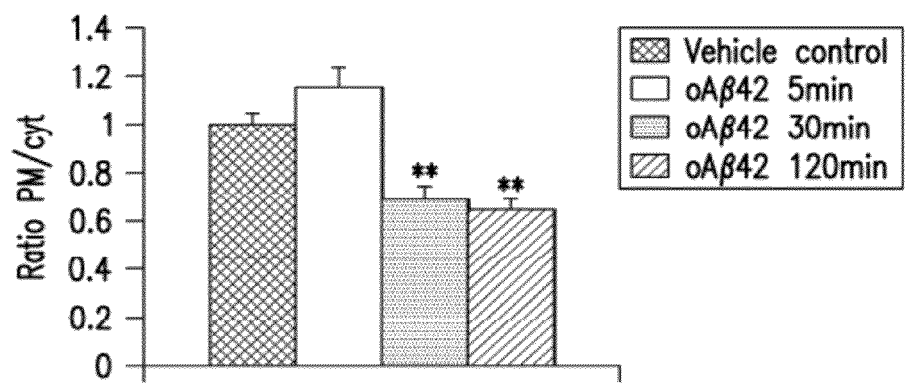
Figure 3C:
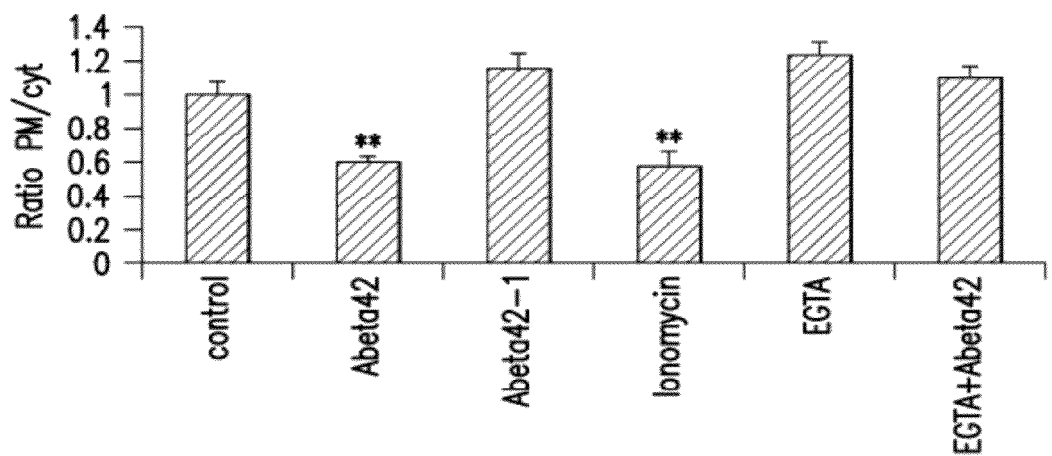

In certain non-limiting embodiments, the present invention provides for an assay system for identifying an agent that inhibits PLD, for example PLD2, wherein the assay system has the features depicted in FIG. 3A-C. For example, the ability of a test agent to modulate the translocation of PLD2, for example a detectably tagged PLD2 (e.g., tagged with a green fluorescent protein) in a cell (e.g., a PC12 cell, in the presence of Ca++ ion) may be tested, where the ability of a test agent to inhibit Aβ42-induced translocation of PLD2 from the cell membrane to the cytoplasm indicates that it is a potential therapeutic agent of the invention and its therapeutic activity may optionally be confirmed in an in vivo test, for example but not limited to, in Tg2576 mice (see FIG. 8).

In non-limiting embodiments, the present invention further provides for an assay system which utilizes cells, preferably neuronal cells, or cell lines (preferably neuronal cell lines) engineered to express a fluorescent version of PLD, preferably PLD2, or a portion thereof which is translocatable from the membrane. The fluorescent protein may be, for example, but not by way of limitation, green fluorescent protein, enhanced green fluorescent protein, yellow fluorescent protein, red fluorescent protein, or any other fluorescent protein known in the art. The PLD may be PLD protein from human, rat or mouse, or a translocatable fragment thereof (see, for example but not by way of limitation, GenBank accession nos. AAH15033, AAH56871, NP002654, EHW90405, EHW90406, AA021120, AAD04197, AAB96656, AAB96655, NP002653, NP001123553, AAH68976, CAB76564, NP150641, AAM48521, BAA24078, U87557, NP032902, NP032901, AAH68144, or NC000077.5). For example, in such assay systems, neuronal cell lines such as but not limited to PC12 cells or N2a cells may be used. Alternatively, non-neuronal cell lines may be used, such as but not limited to CHO. NIH 3t3, HEK293, or HeLa (72).

In a specific, non-limiting embodiment, the pheochromocytoma cell line PC12 may be transfected with a construct encoding a fusion protein comprising a fluorescent protein linked to the entire coding sequence of PLD, preferably PLD2, or a portion of such sequence that undergoes translocation into the cytoplasm upon treatment with Aβ oligomers. After 16-24 hrs, epifluorescent microscopy may be used to visualize the distribution of fluorescent PLD2 at the plasma membrane as compared to the cytoplasm. In control cells, the fluorescence should appear as a rim that borders the cells and is thus concentrated at the plasma membrane. Treatment of cells with oAβ42, where oAβ42 refers to oligomeric Aβ or any other derivative of Aβ42 or other Aβ species, including Aβ40, should induce, within minutes, a significant disappearance of the probe from the plasma membrane and a corresponding increase of the fluorescence levels in the cytoplasm, which should appear more diffuse. This effect may be mimicked by a treatment with ionomycin. In PLD2-transfected cells in the absence of oAβ42, the ability of a test agent to increase the localization of PLD2 at the cell surface may be detected as an increase in the ratio of the fluorescence intensity at the plasma membrane to the average fluorescence intensity of the cytosol.

Accordingly, the present invention provides for a method of identifying an agent that increases cell surface-associated PLD (preferably PLD2) comprising (i) providing a host cell containing a fluorescent PLD (preferably PLD2) sensor; (ii) administering the test agent to the host cell; and (iii) measuring the ratio of the fluorescence at the plasma membrane to the average fluorescence of the cytosol, where an increase in the ratio indicates an increase in PLD (preferably PLD2) levels in the host cell surface.

In an alternative embodiment, the present invention provides for a method of identifying an agent that inhibits a toxic effect of oAβ42, comprising (i) providing a host cell containing a fluorescent PLD (preferably PLD2) sensor; (ii) exposing the host cell to a toxic concentration of oAβ42; (iii) administering the test agent to the host cell; and (iv) measuring the fluorescence at the plasma membrane and in the cytosol, where an increase in the ratio of fluorescence in the plasma membrane versus the cytosol indicates that the test agent inhibits a toxic effect of oAβ42.

In yet another, non-limiting embodiment, the present invention provides for a method of identifying an agent that is an inhibitor of PLD and preferably PLD2 and/or a therapeutic agent for AD, comprising (i) providing a host cell; (ii) administering a test agent to the host cell; and (iii) determining whether administration of the test agent decreases the level of PA 34:2, PA 34:0, and/or GM3 in the host cell, wherein a decrease in the level of PA 34:2, PA 34:0, and/or GM3 indicates that the test agent is an inhibitor of PLD (e.g. PLD2) and may be used to treat AD. See, for example, FIG. 9C-D. For example, the level of PA 34:2, PA 34:0, and/or GM3 in a host cell exposed to the test agent may be compared to the level of PA 34:2, PA 34:0, and/or GM3 in an appropriate control cell. The nomenclature for phospholipids fatty acid (PA) composition are denoted as total chain length:number of unsaturated bonds. In these embodiments, the host cell may be, without limitation, a neuronal cell or cell line or a tissue explant (e.g. cortical tissue) or the host cell may be in a non-human test animal such as a mouse, for example but not limited to a mouse carrying the SwAPP mutation. In one specific non-limiting embodiment the host cell may be a pheochromocytoma cell, e.g. a PC12 cell.

5.3 Methods of Treatment

In certain non-limiting embodiments, the present invention provides for a method of inhibiting synaptic dysfunction, memory impairment and/or neurodegeneration associated with amyloidogenic peptides by administering, to a subject in need of such treatment, an effective amount of an inhibitor of PLD, for example an inhibitor of PLD1 and/or PLD2.

A subject in need of such treatment may be a human or a non-human subject having a PLD enzyme. Said subject may be suffering from synaptic dysfunction, memory impairment and/or neurodegeneration or may be at risk for developing one or more of these conditions due to, for example but not by way of limitation, age, family history, or exposure to a toxic agent.

In certain non-limiting embodiments, the present invention provides for a method of reducing amyloidogenesis (i.e., the production of toxic Aβ species, such as Aβ40 and Aβ42) by blocking or partially blocking the action of phospholipase D enzymes, such as phospholipase D1 and/or phospholipase D2. In certain related non-limited embodiments, the present invention provides for a method of protecting against toxic effects of Aβ42 peptide on a neural cell comprising exposing said cell to an effective amount of a phospholipase D inhibitor.

In certain non-limiting embodiments, the present invention provides for a method of treating (e.g. reducing the symptoms of and/or slowing the progression of and/or reducing the risk of occurrence) a neurodegenerative disease or disorder such as, but not limited to, Alzheimer's disease, Mild Cognitive Impairment, Parkinson's Disease, Huntington's chorea, senile dementia, and/or a prior-related disease, such as Creuzfeld-Jacob disease.

In certain non-limiting embodiments, the present invention provides for a method of inhibiting the progression of memory impairment in a subject, comprising administering, to the subject, an effective amount of a phospholipase D inhibitor. In certain non-limiting embodiments, the present invention provides for a method of reducing the risk of occurrence of memory impairment and/or dementia, comprising administering, to a subject, for example a human subject at least about 40 years old or at least about 50 years old or at least about 60 years old, an effective amount of a PLD inhibitor.

In further non-limiting embodiments, the present invention provides for a method of treating a disorder associated with increased ganglioside levels comprising administering, to a subject in need of such treatment, an effective amount of a PLD inhibitor, preferably a PLD2 inhibitor, so as to ameliorate the clinical condition of the subject and/or decrease the ganglioside level. Non-limiting examples of disorders associated with increased ganglioside levels are GM1 gangliosidosis, Morquio B disease, Tay-Sachs disease, Sandhoff disease, AB variant, and Niemann-Pick disease type C.

PLD inhibitors which may be used in the methods discussed in this section are set forth in section 5.1, above.

A PLD inhibitor may be administered by any suitable route known in the art, including, but not limited to, by oral, subcutaneous, intramuscular, intravenous, intrathecal, inhalation, or rectal administration.

In particular, non-limiting embodiments, the PLD inhibitor is FIPI, administered to achieve a concentration in the cerebrospinal fluid of between about 50 and 2500 nM, or between about 250 and 2000 nM, or between about 250 and 1000 nM. Where the PLD inhibitor is not FIPI, the dose ranges for the (non-FIPI) PLD inhibitor may be determined by multiplying the aforesaid dose ranges for FIPI by the ratio of the EC50 of said PLD inhibitor to the EC50 of FIPI, for example, but not by way of limitation, as measured by an assay described herein, such as the ability of the agent to inhibit oAβ42-induced translocation of PLD from the plasma membrane to the cytoplasm, or to inhibit an oAβ42-induced decrease in PIP2 in cultured primary cortical neurons, or to decrease production of Aβ42 in cultured neurons expressing swAPP, or to improve behavioral performance in an animal model of AD such as Tg2576 mice.

In one particular, non-limiting embodiment, where the PLD inhibitor is compound 56 of FIG. 11C (which is also the Dual PLD1/2 inhibitor 2 of FIG. 11E and compound 2 of FIG. 11F), also known as N-(2-(4-(2-oxo-2,3-dihydro-1H-benzo[d]imidazol-1-yl)piperidin-1-yl)ethyl)-2-napthamide, which has a PLD1 $IC_{50}$ of 81 nM, a PLD2 $IC_{50}$ of 240 nM, a 293-PLD2 $IC_{50}$ of 380 nM, and a Calu-1 $IC_{50}$ of 21 nM, said PLD inhibitor may be administered to achieve a concentration in the cerebrospinal fluid of between about 10 and 2000 nM, or between about 10 and 1000 nM, or between about 10 and 500 nM, or between about 200 and 1000 nM, or between about 200 and 500 nM.

In another particular, non-limiting embodiment, where the PLD inhibitor is compound 13r of FIG. 11J, also, known as (1R,2R)—N—((S)-1-(4-(5-bromo-2-oxo-2,3-dihydro-1H-benzo[d]imidazol-1-yl)piperidin-1-yl)propan-2-yl)-2-phenylcyclopropanecarboxamide, which has a PLD1 $IC_{50}$ of 15 nM, a PLD2 $IC_{50}$ of 1100 nM, a 293-PLD2 $IC_{50}$ of 6400 nM, and a Calu-1 $IC_{50}$ of 3.7 nM, said PLD inhibitor may be administered to achieve a concentration in the cerebrospinal fluid of between about 2 and 10,000 nM, or between about 2 and 200 nM, or between about 2 and 100 nM, or between about 2 and 50 nM, or between about 500 and 8000 nM, or between about 500 and 2000 nM.

In another particular, non-limiting embodiment, where the PLD inhibitor is the PLD2 selective inhibitor compound 9b of FIG. 11K, also, known as N-(2-(4-oxo-1-phenyl-1,3,8-triazaspiro[4,5]decan-8-yl)ethyl)quinoline-3-carboxamide, which has a PLD1 $IC_{50}$ of 20,000 nM, a PLD2 $IC_{50}$ of 500 nM, a 293-PLD2 $IC_{50}$ of 90 nM, and a Calu-1 $IC_{50}$ of 1900 nM, said PLD inhibitor may be administered to achieve a concentration in the cerebrospinal fluid of between about 30 and 1500 nM, or between about 50 and 1000 nM, or between 50 and 800 nM, or between 50 and 600 nM.

In particular, non-limiting embodiments, a PLD inhibitor may be administered once or more daily, once or more weekly, or once or more monthly. Periods of treatment may be continuous or discontinuous.

6. EXAMPLE 1

The domain structure of PLD1/PLD2 is shown in FIG. 1A. Regions I-IV are key determinants of the catalytic domain and HKD signature motifs (II and IV) indicate the consensus sequence HxK(x)4D(x)6GSxN. PLD1 contains an additional region (activation loop, L) that is involved in the regulation of catalytic activity. The transphosphatidylation reaction mediated by PLD enzymes, which leads to the synthesis of phosphatidylethanol (PEtOH) or phosphatidylbutanol (PButOH) in the presence of ethanol and 1-butanol, respectively, is shown in FIG. 1B.

Figure 2A:
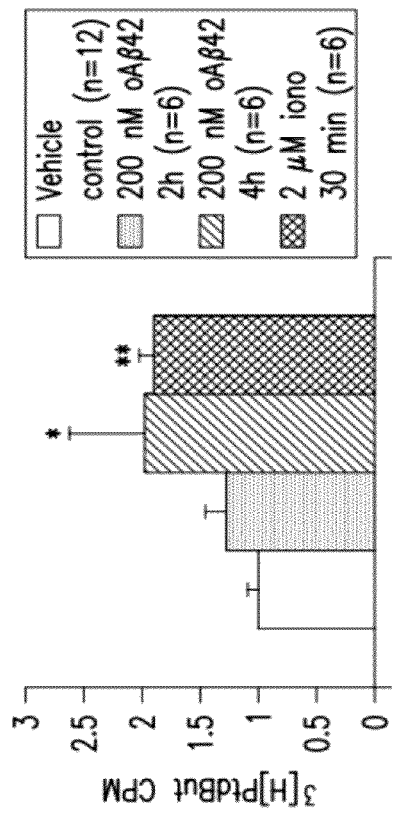
Figure 2B:
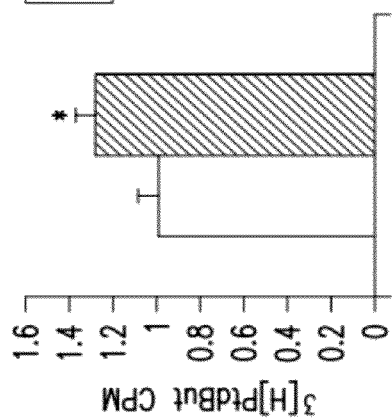
Figure 2C:
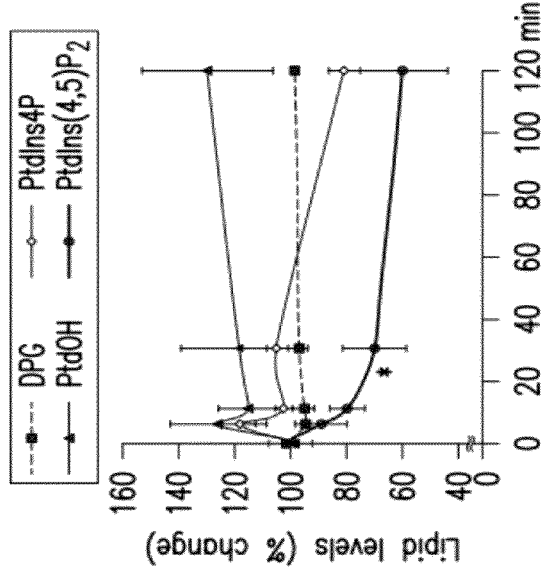
Figure 2D:
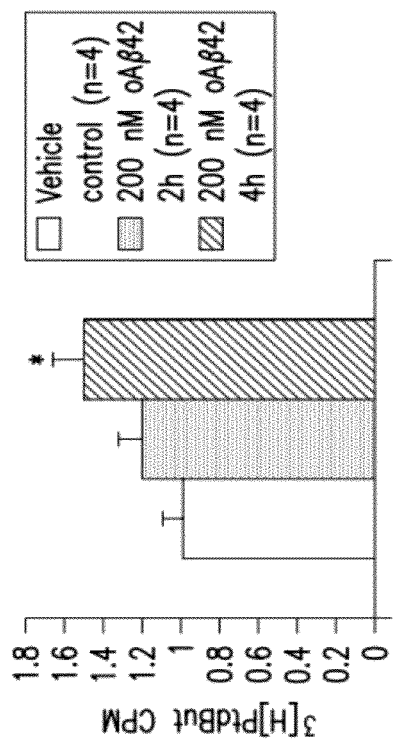

When cultured primary cortical neurons were treated with 200 nM synthetic oligomerized Aβ42 ("oAβ42"), the level of phosphatidic acid (PtdOH) has been observed to increase (FIG. 2A). Further, acute extracellular applications (at 200 nM) of oAβ42 were found to stimulate the enzymatic activity of phospholipase D (PLD) in primary cortical neurons derived from newborn mice (FIG. 2B) and in the neuroblastoma cell line Neuro2A (N2A)(FIG. 2C). Overexpression of the Swedish mutant of amyloid precursor protein (swAPP) in neuroblastoma cell line N2A, which has been shown to lead to increased generation and secretion of Aβ, was also found to stimulate the enzymatic activity of PLD (FIG. 2D).

Figure 2E:
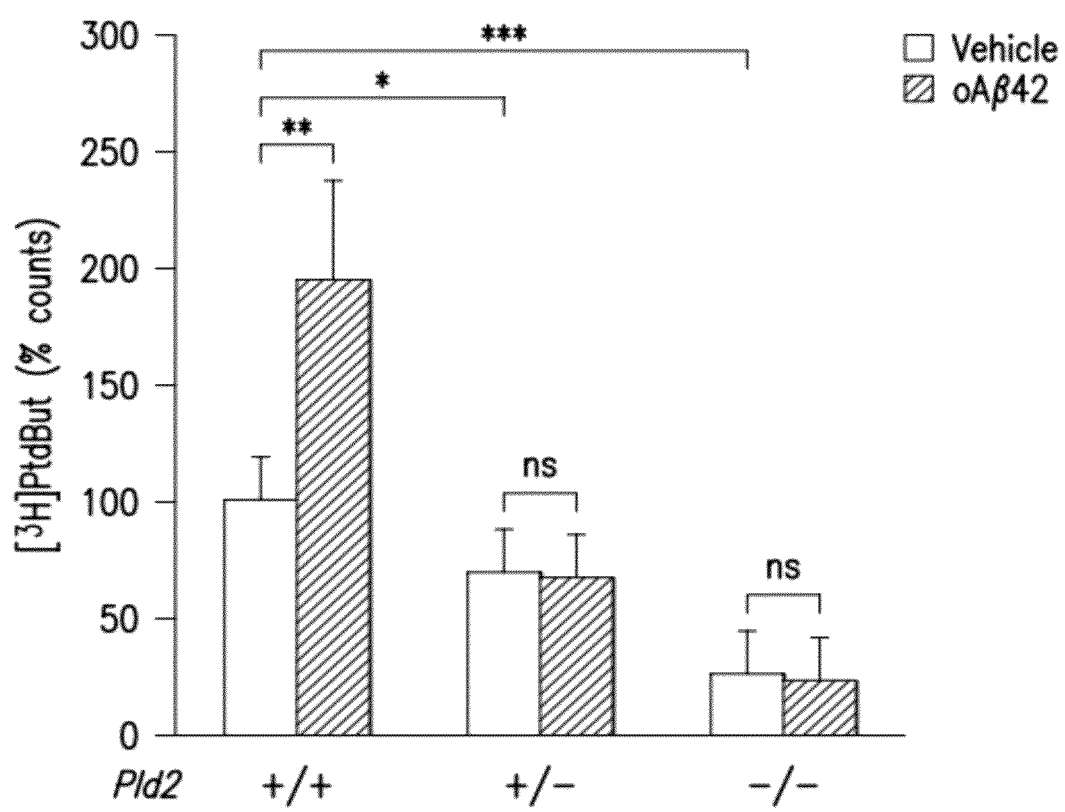

As shown in FIG. 2E, cultured neurons lacking PLD2 do not respond to treatment with Aβ42 oligomers. Primary neuron cortical cultures were labeled with [3H]myristic acid at day 12, treatments were performed at day 15, lipids were subsequently extracted and the ratio [3H]PhosphatidylButanol counts/total counts was used as a measure of PLD activity. Four-hour treatments with vehicle or oAβ42 200 nM were performed prior to PLD activity measurement in Pld2+/+ (n=19 and 12 for vehicle and oAβ42 treatment, resp.), Pld2+/− (n=7), and Pld2−/− (n=5 and 7, resp.).

Figure 3D:
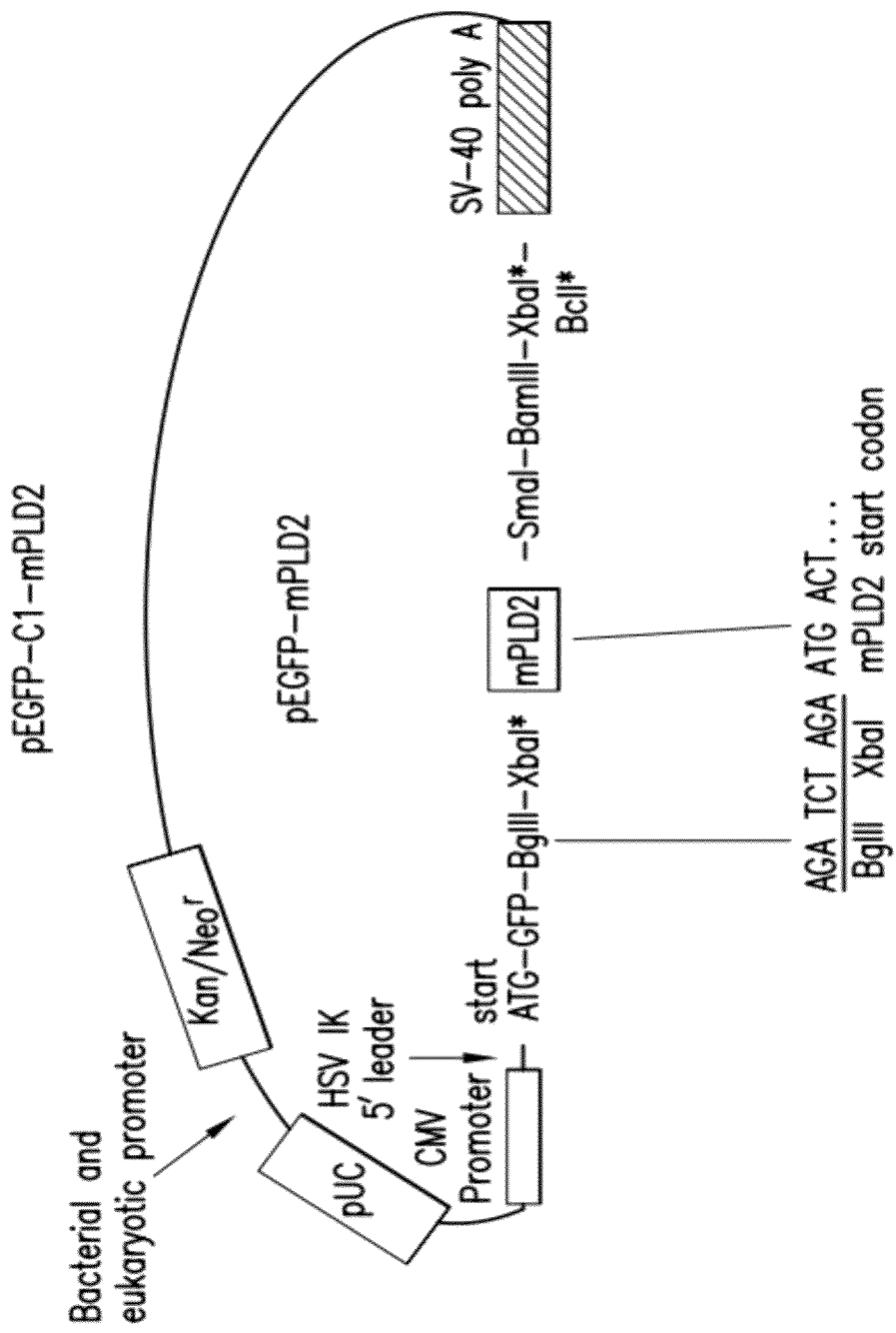

To monitor the cellular location of PLD2, a GFP-tagged PLD2 construct was prepared (FIG. 3D). In preparing the construct, mPLD2 could be excised using XbaI and SmaI sites (there are internal BamHI and BglII sites), although in typical bacterial strains methylation interferes with cutting at the XbaI and BclI site. pEGFP was about 4.7 kb in length, and mPLD2 cDNA was about 3 kb in length. pEGFP (Clontech) was used as it encodes the red-shifted variant of GFP that is optimized for mammalian cells. Genbank accession number of PLD2 (murine) is U87557. The GFP-PLD2 encoding construct was introduced into PC12 cells by Lipofectamine 2000 (see Hammond et al., 1995, J. Biol. Chem. 270:29640-29643; Colley et al., 1997, Current Biology 7:191-201; Sung et al., 1997, EMBO J. 16:4519-4530; Sung et al., 1999, J. Biol. Chem. 274:3659-3666; and Sung et al., 1999, J. Biol. Chem. 274:494-502). Acute extracellular applications (at 200 nM) of oAβ42 lead to a translocation of GFP-tagged phospholipase D2 (PLD2) from the cell surface to the cytoplasm in pheochromocytoma cell line PC12 in a Ca2+-dependent fashion (i.e., the effect if blocked by agents that sequester extracellular Ca2+, such as EGTA) (FIG. 3A-C).

In order to provide an in vivo model system for studying the role of PLD2 in the nervous system, PLD2 "knock out" mice ("PLD2KO mice") were prepared using Cre-LoxP technology. Immunoreactivity to PLD2 was shown to be absent in brain extracts of these mice, indicating that PLD2 is not expressed in the knockout animals (FIG. 4A). Further, total PLD activity in the brains of Pld knockout mice was shown to be reduced by approximately half (FIG. 4B). The PLD2 knockout mice were viable and have not been observed to exhibit obvious anomalies to date.

In a first series of experiments to test the effects of Aβ42 in the PLD2 KO animals, primary cortical neurons of WT and KO mice were harvested, established in culture, and then infected with a swAPP-lentivirus. Expression of full length swAPP in neurons typically results in large amounts of secreted Aβ40 and Aβ42. The resulting Pld2 KO neurons were observed to secrete lower amounts of Aβ40 and Aβ42 compared to wild typecultures (FIG. 5A-B).

Next, the effect of PLD2KO on long term potentiation ("LTP") was tested in hippocampal brain slices made from the KO animals. LTP is a phenomenon that is measured using electrophysiology techniques and that correlates with learning and memory in many instances. Several groups have previously shown that Aβ (and Aβ oligomers in particular) disrupts LTP, potentially providing a basis for cognitive deficits associated with mild cognitive impairment and Alzheimer's disease. As shown in FIG. 6, whereas hippocampi from mice wildtype for PLD2, exposed to oAβ42, showed a reduction of LTP, hippocampi from PLD2KO mice showed normal LTP in the presence of oAβ42.

In order to test the in vivo effects of PLD2KO in the context of Aβ42 overexpression, PLD2KO mice were crossed with swAPP mice. Offspring homozygous and heterozygous for ablation of PLD2 were produced, and then compared with control animals (including swAPP mutant animals having wild-type PLD2) in performance of two behavioral tests. The results of testing in the Contextual Fear Conditioning (FC) paradigm are presented in FIG. 7, and the results of testing in the Radial Arm Water Maze (RAWM) paradigm are presented in FIG. 8. In both of these testing paradigms, genetic inactivation of one or two copies of Pld2 in mice overexpressing swAPP (line Tg2576) ameliorated the learning deficits that are characteristic of Tg2576 (swAPP-expressing) mice.

Figure 9A:
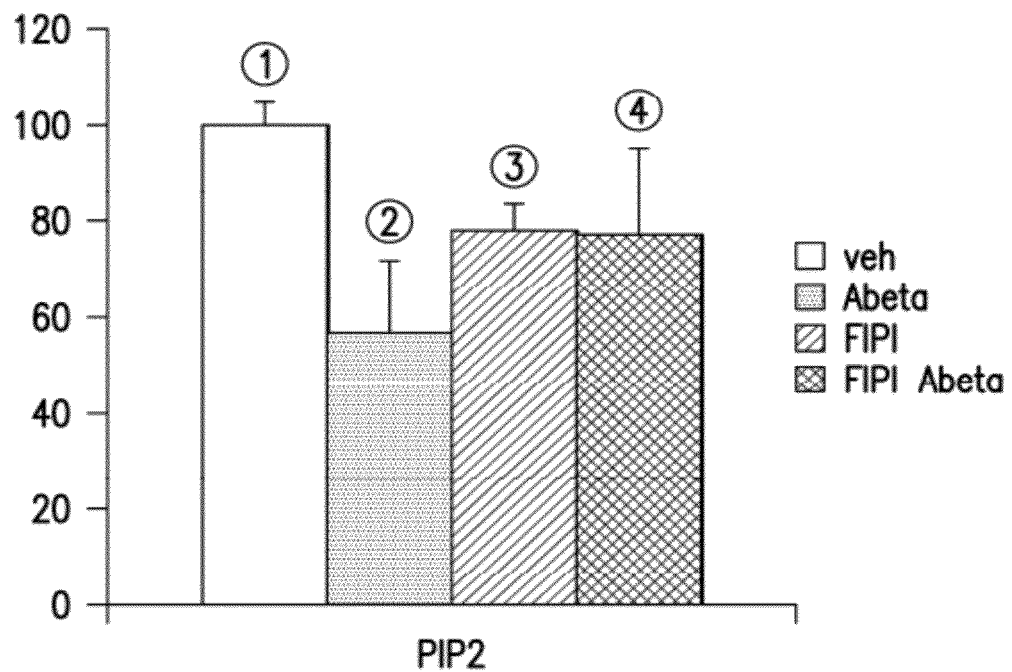

Having demonstrated, in the foregoing experiments, the Aβ42-protective benefits of genetic ablation of PD2, experiments were performed to assess the effects of chemical inhibition of that enzyme. As shown in FIG. 9A, a pharmacological inhibitor of PLD (including PLD2), 5-Fluoro-2-indolyl des-chlorohalopemide ("FIPI"), was found to partially rescue PIP2 deficiency in primary cortical neurons following acute extracellular applications (at 200 nM) of oAβ42. FIPI is an analog of halopemide that was originally characterized in Monovich, L. et al. Optimization of halopemide for phospholipase D2 inhibition. Bioorg Med Chem Lett 17, 2310-2311 (2007) and further characterized by the group of Michael Frohman (Su, W. et al. 5-Fluoro-2-indolyl deschlorohalopemide (FIPI), a phospholipase D pharmacological inhibitor that alters cell spreading and inhibits chemotaxis. Mol Pharmacol 75, 437-446 (2009)).

Figure 9B:
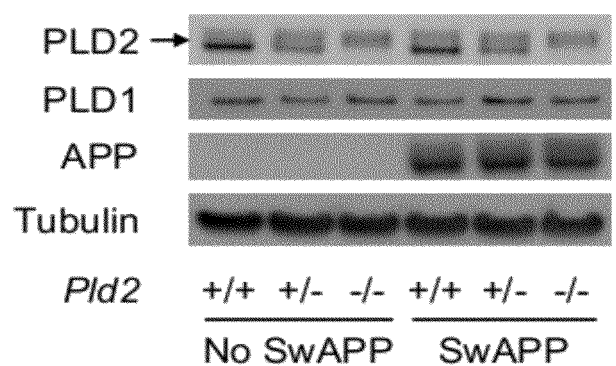
Figure 9C:
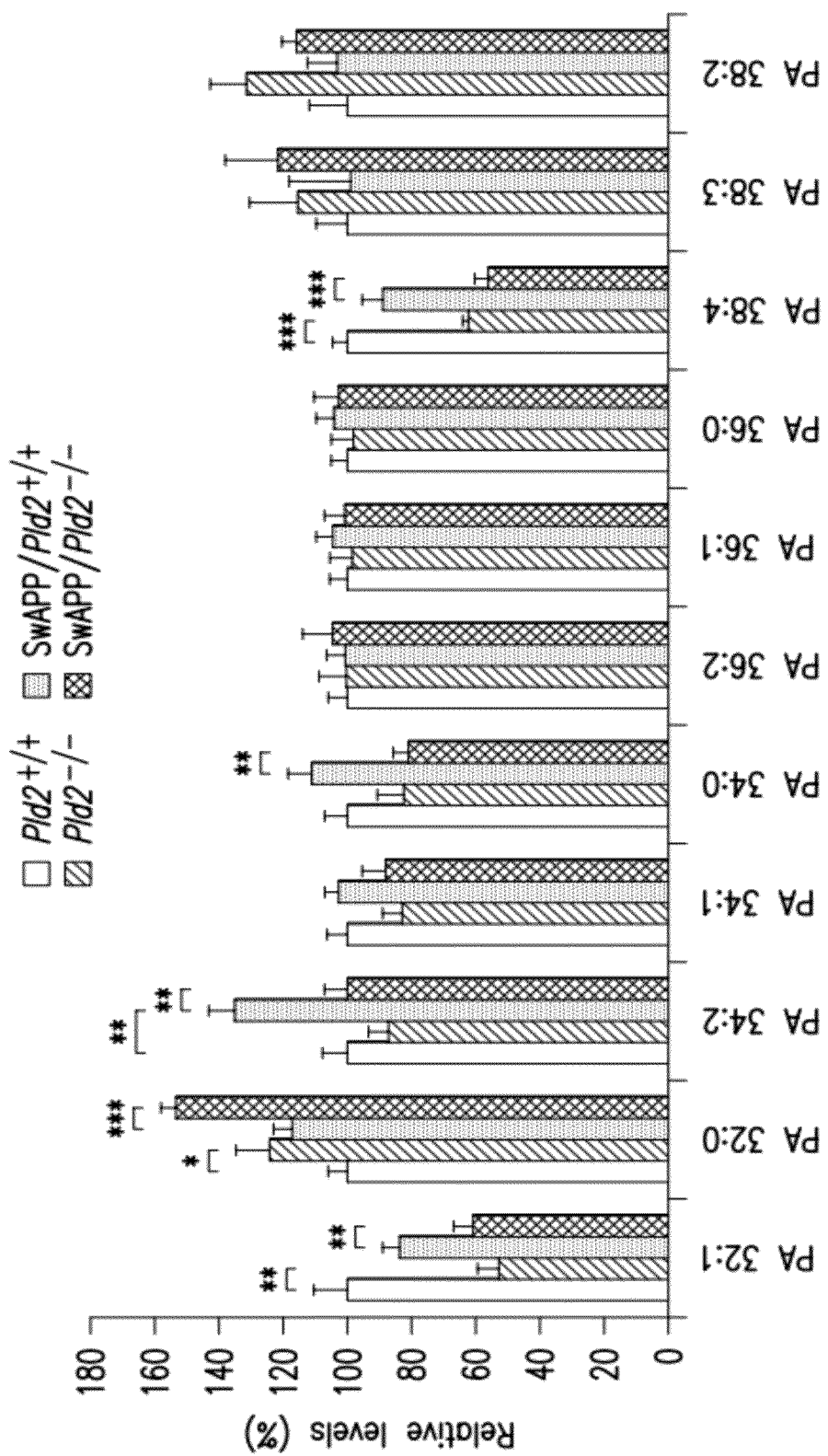
Figure 9D:
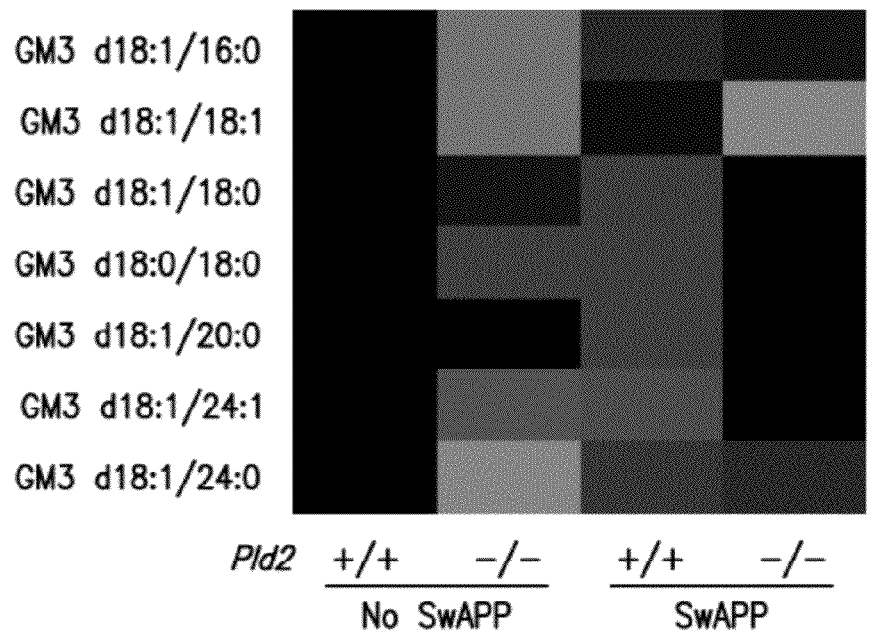
Figure 9E:
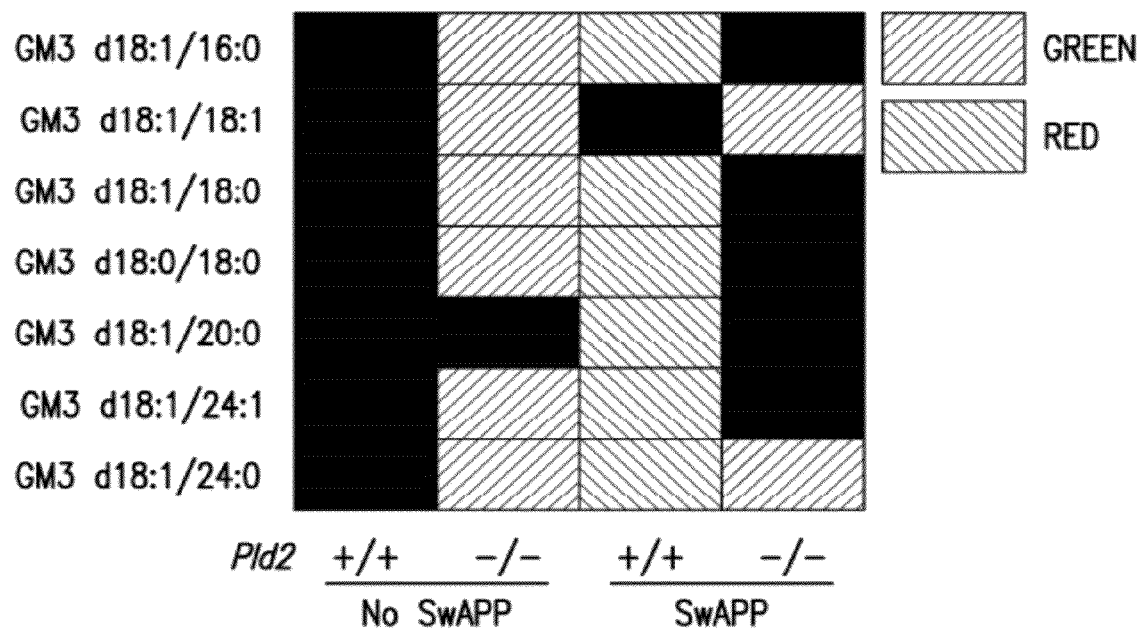

Next, experiments were performed to study the effects of SwAPP overexpression and Pld2 genotypes on PA and ganglioside GM3 levels. As shown in FIG. 9B, protein levels were evaluated by Western blot analysis of PLD2, PLD1, APP and tubulin (representative blots are shown). Forebrain lipids were extracted from Pld2+/+ and Pld2−/− mice with and without the SwAPP transgene and subjected to LC-MS analysis, and the relative amounts of PA species were measured in mutant mice and compared to control mice (Pld2+/+, no SwAPP); the results are shown in FIG. 9C. The PA species 34:2 and 34:0 (arrows) are candidate biomarkers for Alzheimer's disease and their reduction in the Pld2 knockout (KO) indicate that these biomarkers can be used to monitor the action of PLD2 inhibitors. The nomenclature for phospholipids fatty acid composition are denoted as total chain length: number of unsaturated bonds. As shown in FIG. 9D, the glycosphingolipid (ganglioside) GM3 is elevated in the Alzheimer's disease mouse mutant (red color) and can be used as a biomarker for this disease. The levels of GM3 go down in the Pld2 KO (green color). In the SwAPP mutant, ablation of PLD2 restores normal levels of GM3 (black).

Additionally, N2A cells expressing swAPP were found to secrete lower amounts of Aβ42 when treated with FIPI (FIG. 10). Note that because FIPI blocks both PLD1 and PLD2, it is unclear whether the protective effects of the drug involve PLD1, PLD2 or both.

In conclusion, the genetic ablation of PLD2 by itself, both partial and total, does not appear to have substantial effects at the organismal level on knockout mice, and since the genetic ablation of PLD2 confers protection in the setting of various Alzheimer's Disease experimental models, PLD2 emerges as a rational target for pharmacologic inhibition. Similarly, ablation of PLD1 has not been observed to lead to any obvious anomalies, suggesting that therapeutics relying on PLD1 inhibition may also carry therapeutic benefit.

7. EXAMPLE 2

Growing evidence indicates that Alzheimer's disease (AD) is associated with profound changes in the metabolism of lipids and that these changes may be responsible for the perturbation of molecular pathways underlying synaptic dysfunction and cognitive decline. In this study, we have investigated the link between amyloid beta (Abeta) and phosphatidic acid (PtdOH), a key signaling phospholipid that controls multiple cellular processes. We had previously reported that a treatment of cultured neurons with soluble Abeta 1-42 oligomers increases PtdOH levels. Because the phospholipase D (PLD) pathway is a primary source of a bioactive pool of PtdOH, we have focused on this family of lipid enzymes. Accordingly, treatment of cultured neurons and neuroblastoma cells with Abeta 1-42 oligomers as well as expression of the Swedish mutant of APP (swAPP) lead to a significant increase in PLD activity. We also show that Abeta 1-42 oligomer treatment promotes the translocation of PLD2 from the plasma membrane to the cytoplasm, further suggesting that PLD2 lies in the Abeta signaling pathway. To genetically test for the relevance of the PLD pathway in AD, we have generated mice harboring a conditional deletion of the Pld2 gene. Our results indicate that Pld2 ablation, which does not lead to any overt phenotypes, suppresses the synapse-impairing action of Abeta on long-term potentiation (LTP) in hippocampal slices, suggesting that it confers protection against the cytotoxic peptide. Strikingly, our behavioral analysis shows that contextual learning is improved in a transgenic mouse model of AD (swAPP) that either lacks one (swAPP/Pld2+/−) or two copies (swAPP/Pld2−/−) of Pld2. Altogether, these findings suggest that the PLD2 pathway mediates some of the cytotoxic effects of Abeta oligomers and that blocking this pathway may ameliorate AD-linked synaptic dysfunction and cognitive decline.

Various publications are cited herein, the contents of which are hereby incorporated in their entireties.

We claim:

1. A method of treating a neurodegenerative disease selected from the group consisting of Alzheimer's disease, Mild Cognitive Impairment, Parkinson's Disease, Huntington's disease and senile dementia, comprising administering to a subject in need of such treatment, an effective amount of an inhibitor of phospholipase D2, wherein the inhibitor is selected from the group consisting of i) inhibitors depicted in (FIG. 11B-M);

(ii) a halopemide derivative comprising a 2-indolyl moiety, a halogenated piperidinylbenzimidazolone moiety and an S-methyl moiety, or a 1,3,8-triazaspiro[4,5]decan-4-one moiety;

(iii) 5-Fluoro-2-indolyl des-chlorohalopemide ("FIPI");

(iv) N-(2-(4-(2~oxo-2,3-dihydro-1H-benzo[d]imidazol-1-yl)piperidin-1-yl)ethyl)-2-napthamide;

(v) (1R,2R)—N—((S)-1-(4-(5-bromo-2-oxo-2,3-dihydro-1H-benzo[d]imidazol-1-yl)piperidin-1-yl)propan-2-yl)-2-phenylcyclopropanecarboxamide;

(vi) N-(2-(4-oxo-1-phenyl-1,3,8-triazaspiro[4,5]decan-8-yl)ethyl)quinoline-3-carboxamide; and (vii) an inhibitor selected from the group consisting of

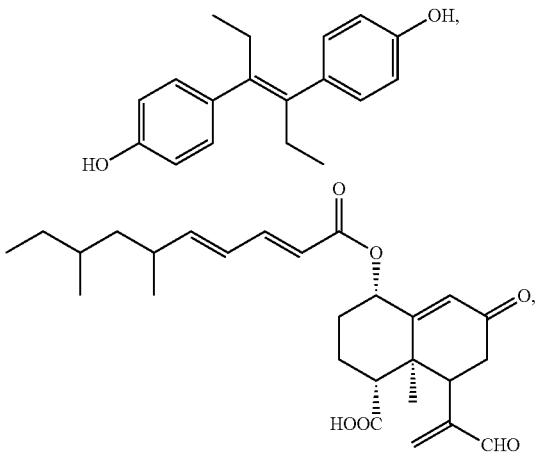

-continued

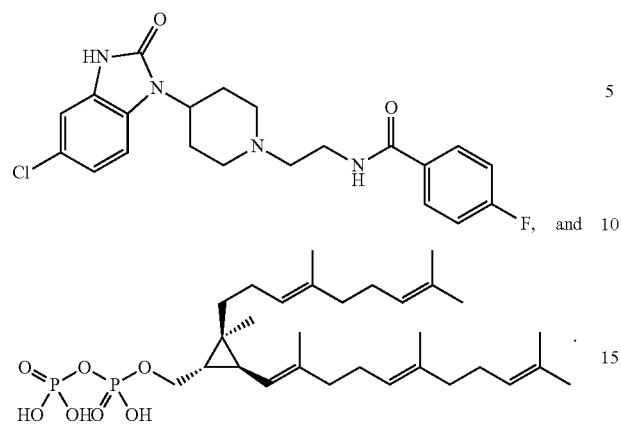

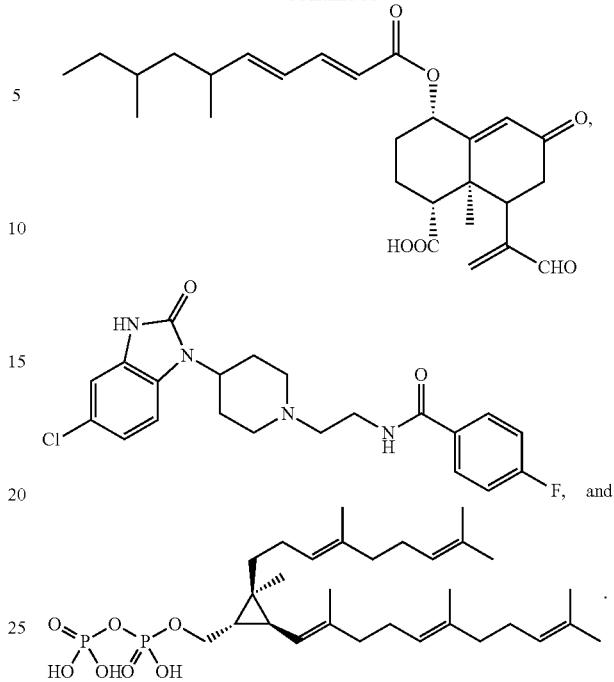

2. A method of protecting against toxic effects of Aβ42 peptide on a neural cell comprising exposing said cell to an effective amount of an inhibitor of phospholipase D2, wherein the inhibitor is selected from the group consisting of
 (i) inhibitors depicted in (FIG. 11B-M);
 (ii) a halopemide derivative comprising a 2-indolyl moiety, a halogenated piperidinyl benzimidazolone moiety and an S-methyl moiety, or a 1,3,8-triazaspiro[4,5]decan-4-one moiety;
 (iii) 5-Fluoro-2-indolyl des-chlorohalopemide ("FIPI");
 (iv) N-(2-(4-(2-oxo-2,3-dihydro-1H-benzo[d]imidazol-1-yl)piperidin-1-yl)ethyl)-2-napthamide;
 (v) (1R,2R)—N—((S)-1-(4-(5-bromo-2-oxo-2,3-dihydro-1H-benzo[d]imidazol-1-yl)piperidin-1-yl)propan-2-yl)-2-phenylcyclopropanecarboxamide;
 (vi) N-(2-(4-oxo-1-phenyl-1,3,8-triazaspiro[4,5]decan-8-yl)ethyl)quinoline-3-carboxamide; and
 (vii) an inhibitor selected from the group consisting of

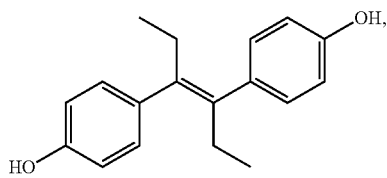

3. The method of claim 1 where the phospholipase D2 inhibitor is a halopemide derivative comprising a 2-indolyl moiety, a halogenated piperidinyl benzimidazolone moiety and an S-methyl moiety, or a 1,3,8-triazaspiro[4,5]decan-4-one moiety.

4. The method of claim 1 where the phospholipase D2 inhibitor is selected from the group consisting of phospholipase D inhibitors depicted in (FIG. 11B-M).

5. The method of claim 1 where the phospholipase D2 inhibitor is 5-Fluoro-2-indolyl des-chlorohalopemide ("FIPI").

6. The method of claim 1 where the phospholipase D2 inhibitor is N-(2-(4-(2-oxo-2,3-dihydro-1H-benzo[d]imidazol-1-yl)piperidin-1-yl)ethyl)-2-napthamide.

7. The method of claim 1 where the phospholipase D2 inhibitor is (1R,2R)—N—((S)-1-(4-(5-bromo-2-oxo-2,3-dihydro-1H-benzo[d]imidazol-1-yl) piperidin-1-yl)propan-2-yl)-2-phenylcyclopropanecarboxamide.

8. The method of claim 1 where the phospholipase D2 inhibitor is N-(2-(4-oxo-1-phenyl-1,3,8-triazaspiro[4,5]decan-8-yl)ethyl)quinoline-3-carboxamide.

* * * * *